US008211187B2

(12) United States Patent
Slemker et al.

(10) Patent No.: US 8,211,187 B2
(45) Date of Patent: Jul. 3, 2012

(54) ELEVATED VACUUM LOCKING SYSTEM

(75) Inventors: Tracy C. Slemker, Clayton, OH (US);
Paul L. Galloway, Clayton, OH (US);
Robert Hoskins, Springboro, OH (US);
Steven Steinbarger, Wilmington, OH (US)

(73) Assignee: Prosthetic Design, Inc., Clayton, OH (US)

( * ) Notice: Subject to any disclaimer, the term of this patent is extended or adjusted under 35 U.S.C. 154(b) by 45 days.

(21) Appl. No.: 12/897,807

(22) Filed: Oct. 5, 2010

(65) Prior Publication Data

US 2011/0022183 A1 Jan. 27, 2011

Related U.S. Application Data

(63) Continuation-in-part of application No. 12/481,015, filed on Jun. 9, 2009, now Pat. No. 7,927,377.

(60) Provisional application No. 61/131,457, filed on Jun. 9, 2008.

(51) Int. Cl.
*A61F 2/80* (2006.01)

(52) U.S. Cl. ........................................................ 623/34

(58) Field of Classification Search ............... 623/32–37
See application file for complete search history.

(56) References Cited

U.S. PATENT DOCUMENTS

| 5,702,489 | A  | * | 12/1997 | Slemker        | 623/34 |
| 6,106,559 | A  | * | 8/2000  | Meyer          | 623/33 |
| 6,334,876 | B1 | * | 1/2002  | Perkins        | 623/34 |
| 6,361,569 | B1 | * | 3/2002  | Slemker et al. | 623/33 |
| 6,926,742 | B2 | * | 8/2005  | Caspers et al. | 623/34 |

* cited by examiner

*Primary Examiner* — Bruce E Snow
(74) *Attorney, Agent, or Firm* — Baker & Hostetler LLP

(57) ABSTRACT

Elevated vacuum locking systems for prosthetic limbs are disclosed. Some example embodiments may include a manifold mounted to the exterior of the distal end of a socket and may include a cavity adapted to receive a distal end of a plunger pin when the patient's residual limb and a liner are installed into the socket. Some example manifolds may include a through passage fluidicly connecting an interior of the cavity to a fitting mounted on an exterior of the manifold and/or a spool valve arranged to selectively vent the cavity to atmosphere via the through passage and a vent hole. The spool valve may be axially slidable between an open position and a shut position within a channel integrally formed with the manifold.

9 Claims, 27 Drawing Sheets

ELEVATED VACUUM LOCKING SYSTEM

CROSS REFERENCE TO RELATED APPLICATIONS

This application is a continuation-in-part of application Ser. No. 12/481,015, filed Jun. 9, 2009 U.S. Pat. No. 7,927,377, which claims the benefit of provisional Application No. 61/131,457 filed Jun. 9, 2008, which are incorporated by reference.

BACKGROUND

The present disclosure is directed to systems for releasably coupling a prosthetic device to the residual limb of an amputee. More specifically, the present disclosure is directed to devices utilizing integrated vacuum and mechanical coupling to provide improved retention and comfort for a prosthetic device including a socket.

SUMMARY

An exemplary elevated vacuum locking system for prosthetic limb may include a plunger pin mounted to a flexible liner and including a through passage between a location proximate the exterior of the liner and a distal end of the plunger pin; a locking mechanism mounted within the distal end of a socket; a manifold mounted to the exterior of the distal end of the socket and including a cavity adapted to receive the distal end of the plunger pin when the patient's residual limb and the liner are installed into the socket, the manifold including a through passage connecting an interior of the cavity to an exterior fitting; and a vacuum pump operative to withdraw air from the interior of the socket via the through passage of the plunger pin, the cavity, and the through passage of the manifold.

In an aspect, a prosthetic limb assembly may include a flexible liner shaped to accept a portion of a patient's residual limb, the flexible liner including an interior and an exterior; a plunger pin mounted to a distal end of the flexible liner, the plunger pin including at least one through passage providing fluidic communication between a location proximate the exterior of the liner and a distal end of the plunger pin; a socket shaped to receive the liner and the patient's residual limb, the socket including a socket interior, a proximal opening for receiving the residual limb, and a distal end including a through hole; a locking mechanism mounted within the distal end of the socket and including a central opening sized to receive the plunger pin, the locking mechanism releasably engaging the plunger pin when the residual limb and the liner are inserted into the socket; a manifold mounted to the exterior of the distal end of the socket, the manifold including a cavity aligned with the through hole in the distal end of the socket, the cavity being adapted to receive the distal end of the plunger pin when the patient's residual limb and the liner are installed into the socket, and the manifold including a through passage fluidicly connecting an interior of the cavity to a fitting mounted on an exterior of the manifold; and a vacuum pump operatively connected to the fitting such that the vacuum pump is operative to withdraw air from the interior of the socket via the through passage of the plunger pin, the cavity, and the through passage of the manifold.

In a detailed embodiment, a prosthetic limb assembly may include a cushion mounted on a proximal surface of the locking mechanism, the cushion including an aperture aligned with the central opening of the locking mechanism and the cushion sealingly engaging the interior of the socket. In a detailed embodiment, the plunger pin may include a ratchet portion between the liner and the distal end of the plunger pin. In a detailed embodiment, the plunger pin may include a flange interposing the liner and the ratchet portion. In a detailed embodiment, the plunger pin through passage may include a lateral through passage within the flange fluidicly connected to a longitudinal through passage extending from the lateral through passage to the distal end of the plunger pin. In a detailed embodiment, the plunger pin may include a gasket interposing the flange and the locking mechanism when the residual limb and the liner are installed in the socket, the gasket providing a sealed connection between the flange and the locking mechanism.

In a detailed embodiment, the cushion may include at least one flexible rim circumferentially surrounding the cushion, the at least one rim sealingly engaging an inner surface of the socket. In a detailed embodiment, the manifold may include a substantially planar portion mounted to the distal end of the socket and a distally extending projection, the cavity extending from a proximal end of the planar portion and into the projection. In a detailed embodiment, a prosthetic limb assembly may include at least one fastener extending through the manifold, through the socket wall, and into the locking mechanism.

In a detailed embodiment, the manifold may include an integral pyramid coupling. In a detailed embodiment, the pyramid coupling may be adjustable relative to the socket in at least one of anterior-posterior and medial-lateral directions. In a detailed embodiment, an angular orientation of the pyramid coupling may be rotatably adjustable relative to the socket.

In a detailed embodiment, the manifold may include an integral pyramid receiver. In a detailed embodiment, the pyramid receiver may be adjustable relative to the socket in at least one of anterior-posterior and medial-lateral directions. In a detailed embodiment, an angular orientation of the pyramid receiver may be rotatably adjustable relative to the socket.

In a detailed embodiment, a prosthetic limb assembly may include a gasket interposing the manifold and the distal end of the socket. In a detailed embodiment, a prosthetic limb assembly may include a gasket interposing the distal surface of the locking mechanism and the inside distal surface of the socket. In a detailed embodiment, a prosthetic limb assembly may include a gasket interposing the plunger pin and the manifold.

In an aspect, a plunger pin for a prosthetic limb may include a generally cylindrical body having proximal and distal ends; a liner engagement portion adjacent to the proximal end; a locking mechanism engagement portion distal from the proximal end; a flange interposing the liner engagement portion and the locking mechanism engagement portion, the flange extending radially beyond the cylindrical body; an axial through passage extending within the cylindrical body from the distal end to proximate the flange; and at least one radial through passage extending from an edge of the flange to the axial through passage; where the axial through passage and the at least one radial through passage are fluidicly connected within the generally cylindrical body.

In a detailed embodiment, the liner engagement portion may include threads sized to engage corresponding threads on a distal end of a flexible liner sized and shaped to accept a patient's residual limb.

In a detailed embodiment, the locking mechanism engagement portion may include a plurality of circumferential protrusions and recesses. In a detailed embodiment, at least one of the circumferential protrusions and recesses may be tapered.

In a detailed embodiment, a plunger pin may include a gasket surrounding the cylindrical body and adjacent to a distal surface of the flange. In a detailed embodiment, the lateral through passage may include a plurality of lateral through passages fluidicly connected to the longitudinal through passage.

In an aspect, a manifold for a prosthetic limb may include a generally planar body having a first side, a second side, and a plurality of edges; a projection extending generally perpendicularly from the second side of the flat body; a cavity having an opening on the first side of the planar body, the cavity extending within the projection; and a passage fluidicly connecting the cavity to one of the plurality of edges of the flat body.

In a detailed embodiment, a manifold may include a fitting for coupling to a length of tubing, the fitting being located on the second side of the flat body, where the fitting is fluidicly connected to the passage. In a detailed embodiment, a manifold may include a fitting located on the one of the plurality of edges proximate the passage.

In a detailed embodiment, a manifold may include a first annular groove adjacent to and coaxial with the first surface and the cavity. In a detailed embodiment, a manifold may include a second groove on the first surface, the groove circumscribing the cavity and the first groove. In a detailed embodiment, a manifold may include at least one through hole extending from the first surface to the second surface. In a detailed embodiment, a manifold may include a gasket seated within at least one of the first groove and the second groove.

In a detailed embodiment, the projection may include a pyramid coupling. In a detailed embodiment, the projection may include a pyramid receiver.

In an aspect, a method of donning a prosthetic limb may include providing a prosthetic limb having a socket sized and shaped to receive a patient's residual limb, the socket including a locking mechanism including a central opening mounted in a distal end of an interior of the socket; providing a flexible liner, the flexible liner including a distally-mounted plunger pin extending therefrom, the plunger pin including a longitudinal through passage extending from a distal end of the plunger pin to proximate the flexible liner; providing a vacuum pump fluidicly coupled to a manifold mounted to a distal exterior surface of the socket, the manifold including a cavity aligned with the central opening of the locking mechanism; providing a sealing sleeve proximate a proximal end of the socket; inserting the patient's residual limb into the flexible liner; inserting the patient's residual limb and the flexible liner into the socket such that the plunger pin enters a central opening in the locking mechanism and the locking mechanism releasably engages the plunger pin; placing the sealing sleeve to create a sealed connection between the flexible liner and the proximal end of the socket; and operating the vacuum pump to withdraw air from within the socket via the longitudinal through passage.

In a detailed embodiment, the plunger pin may include a radially extending flange located proximate the liner, the flange including a lateral through passage fluidicly connected to the longitudinal through passage; and the step of operating the pump may include withdrawing air from within the socket via the lateral through passage and the longitudinal through passage. In a detailed embodiment, the plunger pin may include a first gasket adjacent to a distal surface of the flange; and the step of inserting the patient's residual limb and the flexible liner into the socket may include engaging the first gasket with a proximal surface of the locking mechanism. In a detailed embodiment, the cavity may include a second gasket; and the step of inserting the patient's residual limb and the flexible liner into the socket may include engaging the plunger pin and the second gasket.

In an aspect, a prosthetic limb assembly may include a flexible liner shaped to accept a portion of a patient's residual limb, the flexible liner including an interior and an exterior; a plunger pin mounted to a distal end of the flexible liner, the plunger pin including at least one through passage providing fluidic communication between a location proximate the exterior of the liner and a distal end of the plunger pin; a socket shaped to receive the liner and the patient's residual limb, the socket including a socket interior, a proximal opening for receiving the residual limb, and a distal end including a through hole; a locking mechanism mounted within the distal end of the socket and including a central opening sized to receive the plunger pin, the locking mechanism releasably engaging the plunger pin when the residual limb and the liner are inserted into the socket; a manifold mounted to the exterior of the distal end of the socket, the manifold including a cavity aligned with the through hole in the distal end of the socket, the cavity being adapted to receive the distal end of the plunger pin when the patient's residual limb and the liner are installed into the socket, and a through passage fluidicly connecting an interior of the cavity to a fitting mounted on an exterior of the manifold; and a spool valve arranged to selectively vent the cavity to an ambient atmosphere via the through passage and a vent hole, the spool valve being axially slidable between an open position and a shut position within a channel provided in a valve housing integrally formed with the manifold to selectively vent the cavity via the vent hole and fluidicly isolate the cavity from the vent hole. The fitting may be configured to be connected to a vacuum pump for withdrawing air from the interior of the socket via the through passage of the plunger pin, the cavity, and the through passage of the manifold.

In a detailed embodiment, the spool valve may include an open button and a shut button; pressing the open button may slide the spool valve to the open position; and/or pressing the shut button may slide the spool valve to the shut position. In a detailed embodiment, the spool valve may include an open actuator including a first detent configured to engage a spring-biased ball when the spool valve is in the open position and a second detent configured to engage the spring-biased ball when the spool valve is in the shut position.

In a detailed embodiment, the spool valve may include a piston including a face arranged to form a sealed interface with the channel when the spool valve is in the shut position. In a detailed embodiment, the spool valve may include an open actuator including an extension arranged to press against the face of the piston to prevent the face from forming the sealed interface when the spool valve is in the open position.

In a detailed embodiment, the valve housing may be monolithically integrated with the manifold. In a detailed embodiment, a prosthetic limb assembly may include at least one fastener extending through the manifold, through the socket wall, and into the locking mechanism.

In a detailed embodiment, the fitting may include a one-way valve oriented to permit air to vent from an interior of the fitting to the ambient atmosphere and to prevent air from entering the interior of the fitting from the ambient atmosphere. In a detailed embodiment, the fitting may include a one-way valve oriented to permit air to enter an interior of the fitting from the ambient atmosphere when a pressure differential between the ambient atmosphere and the interior of the fitting exceeds a setpoint.

In an aspect, a manifold assembly for a prosthetic limb may include a generally planar body having a first side, a second side, and a plurality of edges; a cavity having an opening on the first side of the generally planar body, the cavity extending within the generally planar body; a passage fluidicly connecting the cavity to a valve housing integrally formed with the generally planar body generally along one of the plurality of edges of the generally planar body, the valve body including a vent hole; a spool valve assembly slidably mounted within a channel extending through the valve housing, the spool valve assembly being configured to selectively vent the passage to atmosphere via the vent hole and to isolate the vent hole from the passage; and a fitting fluidicly connected to the passage, the fitting being configured to fluidicly couple to a vacuum device.

In a detailed embodiment, the valve housing and the generally planar body may be monolithic.

In a detailed embodiment, the fitting may extend generally perpendicularly from the second side of the generally planer body approximate the valve housing. In a detailed embodiment, the channel may be generally parallel to the first side and the second side and generally orthogonal to the fitting.

In a detailed embodiment, the fitting may house a spring configured to bias a ball against at least one detent in an actuator in the spool valve assembly.

In a detailed embodiment, the actuator may include an open actuator including an open button; the at least one detent may include a first detent configured to engage the ball when the spool valve is in an open position in which the spool valve vents the passage to atmosphere via the vent hole; and/or the at least one detent may include a second detent configured to engage the ball when the spool valve is in a shut position in which the spool valve isolates the vent hole from the passage. In a detailed embodiment, the open actuator may include an extension arranged to press against a piston when the spool valve is in the open position; the piston may be spring-biased to form a sealed interface with the channel when the spool valve is in the shut position; and/or, in the open position, the extension may hold the piston out of sealed engagement with the channel.

In an aspect, a method of donning a prosthetic limb may include providing a prosthetic limb having a socket sized and shaped to receive a patient's residual limb, the socket including a locking mechanism including a central opening mounted in a distal end of an interior of the socket; providing a flexible liner, the flexible liner including a distally-mounted plunger pin extending therefrom, the plunger pin including a longitudinal through passage extending from a distal end of the plunger pin to proximate the flexible liner; providing a vacuum pump fluidicly coupled to a manifold mounted to a distal exterior surface of the socket, the manifold including a cavity aligned with the central opening of the locking mechanism, and an integrally formed valve housing comprising a channel in which a spool valve is slidably mounted, the spool valve being arranged to selectively vent the cavity to atmosphere via a vent hole in an open position and to isolate the vent hole from the cavity in a shut position; inserting the patient's residual limb into the flexible liner; sliding the spool valve to the open position; inserting the patient's residual limb and the flexible liner into the socket such that the plunger pin enters a central opening in the locking mechanism and the locking mechanism releasably engages the plunger pin; sliding the spool valve to the shut position; and operating the vacuum pump to withdraw air from within the socket via the longitudinal through passage.

In a detailed embodiment, a method may include sliding the spool valve to the open position; releasing the locking mechanism from the plunger pin; and/or withdrawing the patient's residual limb and the flexible liner from the socket. In a detailed embodiment, the integrally formed valve housing may be monolithically formed with the manifold.

In a detailed embodiment, sliding the spool valve to the open position may include pressing an open button. In a detailed embodiment, pressing the open button may include overcoming a spring force associated with a spring-biased piston of the spool valve to open a sealed interface between the piston and the channel, thereby fluidicly connecting the vent hole and the cavity.

In a detailed embodiment, sliding the spool valve to the shut position may include pressing a close button.

In an aspect, a prosthetic limb assembly may include a flexible liner shaped to accept a portion of a patient's residual limb, the flexible liner including an interior and an exterior; a plunger pin mounted to a distal end of the flexible liner, the plunger pin including at least one through passage providing fluidic communication between a location proximate the exterior of the liner and a distal end of the plunger pin; a socket shaped to receive the liner and the patient's residual limb, the socket including a socket interior, a proximal opening for receiving the residual limb, and a distal end including a through hole; a locking mechanism mounted within the distal end of the socket and including a central opening sized to receive the plunger pin, the locking mechanism releasably engaging the plunger pin when the residual limb and the liner are inserted into the socket; a manifold mounted to the exterior of the distal end of the socket, the manifold including a cavity aligned with the through hole in the distal end of the socket, the cavity being adapted to receive the distal end of the plunger pin when the patient's residual limb and the liner are installed into the socket, and a through passage fluidicly connecting an interior of the cavity to a fitting mounted on an exterior of the manifold; and a valve arranged to selectively vent the cavity to an ambient atmosphere via the through passage and a vent hole, where the fitting may include a one-way valve oriented to permit air to vent from an interior of the fitting to the ambient atmosphere and to prevent air from entering the interior of the fitting from the ambient atmosphere.

In a detailed embodiment, the one-way valve may include a duck bill valve. In a detailed embodiment, the valve may include a spool valve, the spool valve being axially slidable between an open position and a shut position within a channel provided in a valve housing integrally formed with the manifold to selectively vent the cavity via the vent hole and fluidicly isolate the cavity from the vent hole.

BRIEF DESCRIPTION OF THE DRAWINGS

The detailed description refers to the following figures in which.

DETAILED DESCRIPTION

Figure 1:
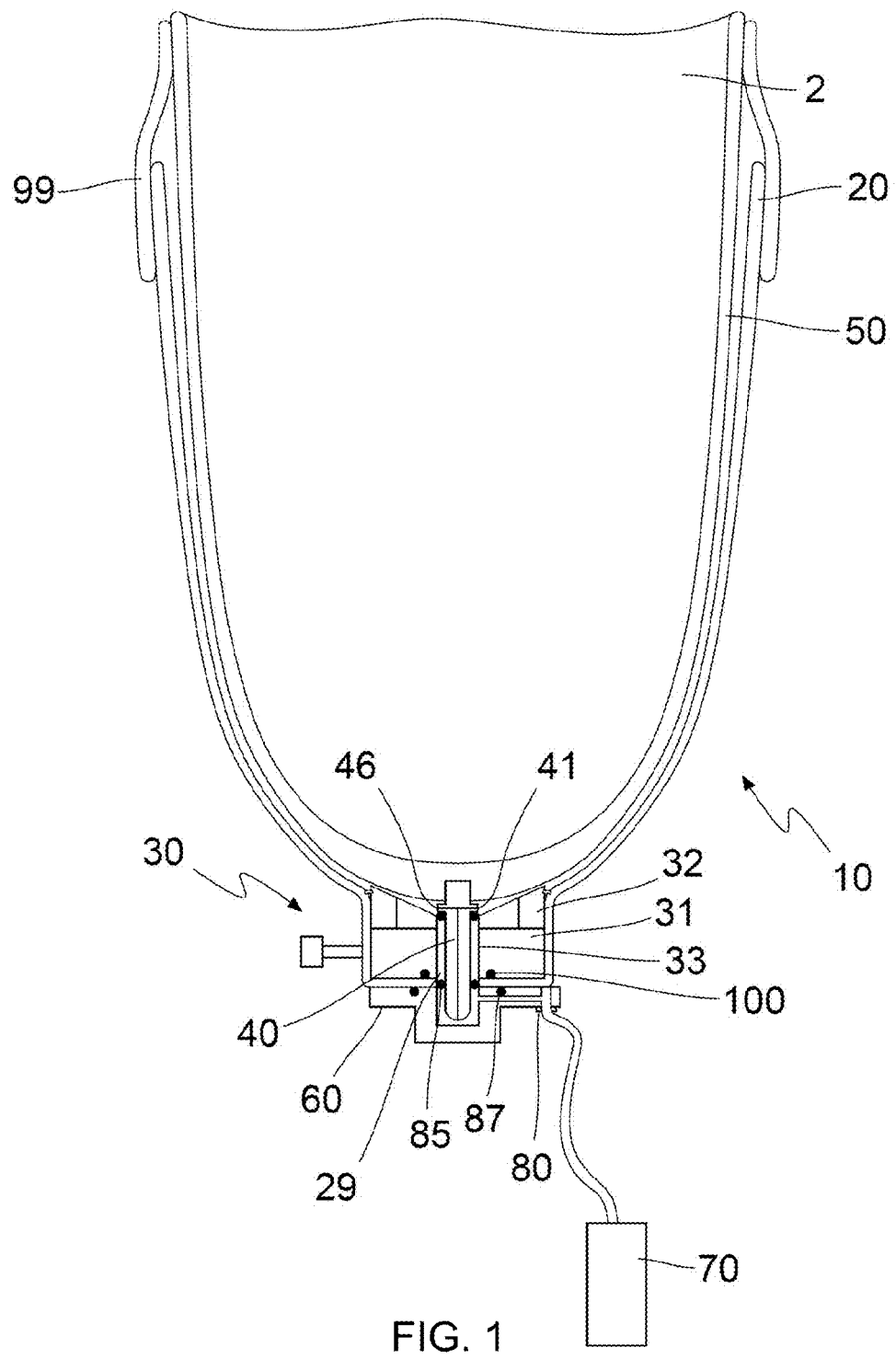
FIG. 1 is a cross-sectional view of an exemplary elevated vacuum locking system.
Figure 2:
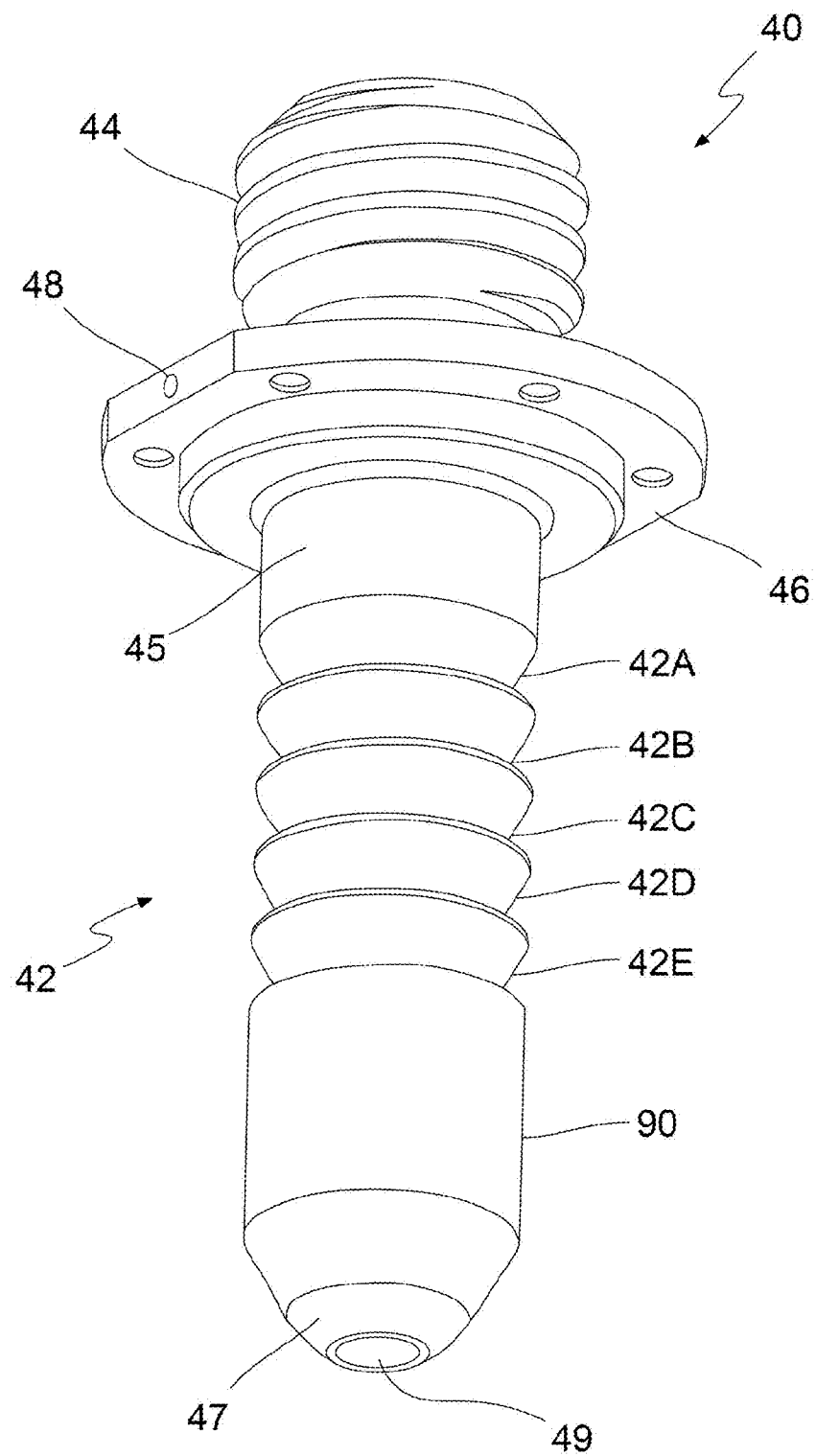
FIG. 2 is a perspective view of an exemplary plunger pin.

As shown in FIG. 1, an exemplary elevated vacuum locking system 10 may include a socket 20 for receiving a portion of an amputee's residual limb 2, a locking mechanism 30 for releasably engaging a plunger pin 40 extending from a flexible liner 50 which interposes residual limb 2 and the socket 20, a manifold 60, a vacuum device 70, and/or a sealing sleeve 99. In an exemplary embodiment, socket 20 may be constructed from a rigid polymer, flexible liner 50 may be formed from a flexible silicone compound, and/or plunger pin 40 and manifold 60 may be constructed from metal, for example.

An exemplary liner 50 may include a fabric shell, such as a nylon/cotton sheath/sock that may provide a wicking action to assist in removing air from the socket when the vacuum source is applied. The wick may be provided by a cloth covering on the liner and/or a sock that that may be put on over a liner with no cover, for example. If vacuum is applied without this wick, the liner may seal to the inside surface of the socket and a large portion of air may remain proximal to this sealing point. Using the wick may aid in evacuation of substantially all of the air from the interior of the socket and/or may aid in ensuring that a seal occurs between the sealing sleeve and the portion of the liner proximal to the socket trim line.

FIGS. 2-5 depict an exemplary plunger pin 40, which may include a ratchet portion 42 including one or more grooves 42A, 42B, 42C, 42D, 42E arranged circumferentially for releasably engaging the locking mechanism 30. The grooves 42A, 42B, 42C, 42D, 42E may include tapered portions to allow the ratchet portion 42 of the plunger pin 40 to slide relative to a spring-loaded latch in one direction while preventing movement relative to the latch in the opposite direction. In an exemplary embodiment, insertion of the ratchet portion 42 into the locking mechanism 30 may produce one or more audible "clicks," which may indicate positive engagement of the locking mechanism 30 and the plunger pin 40.

Plunger pin 40 may include a threaded end 44 for engaging the flexible liner 50. For example, the threaded end 44 may engage a threaded boss formed within the distal end of flexible liner 50. It is within the scope of the disclosure to utilize other methods of coupling plunger pin 40 to liner 50.

A flange 46 may interpose ratchet portion 42 and threaded end 44. As shown in FIG. 1, flange 46 may be located generally between the locking mechanism 30 and liner 50 when liner 50 is inserted into socket 20.

Figure 3:
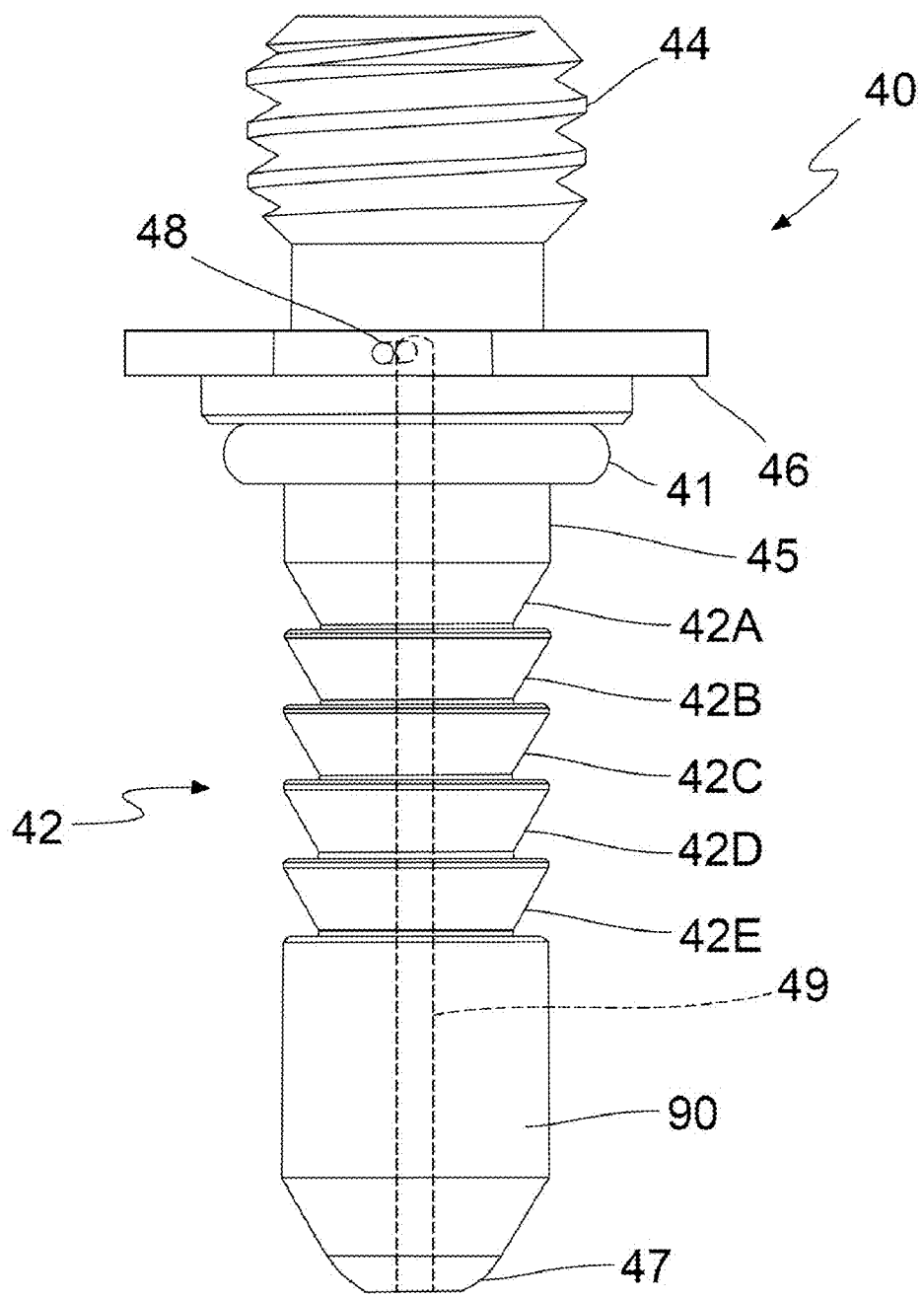
FIG. 3 is an elevation view of an exemplary plunger pin.
Figure 4:
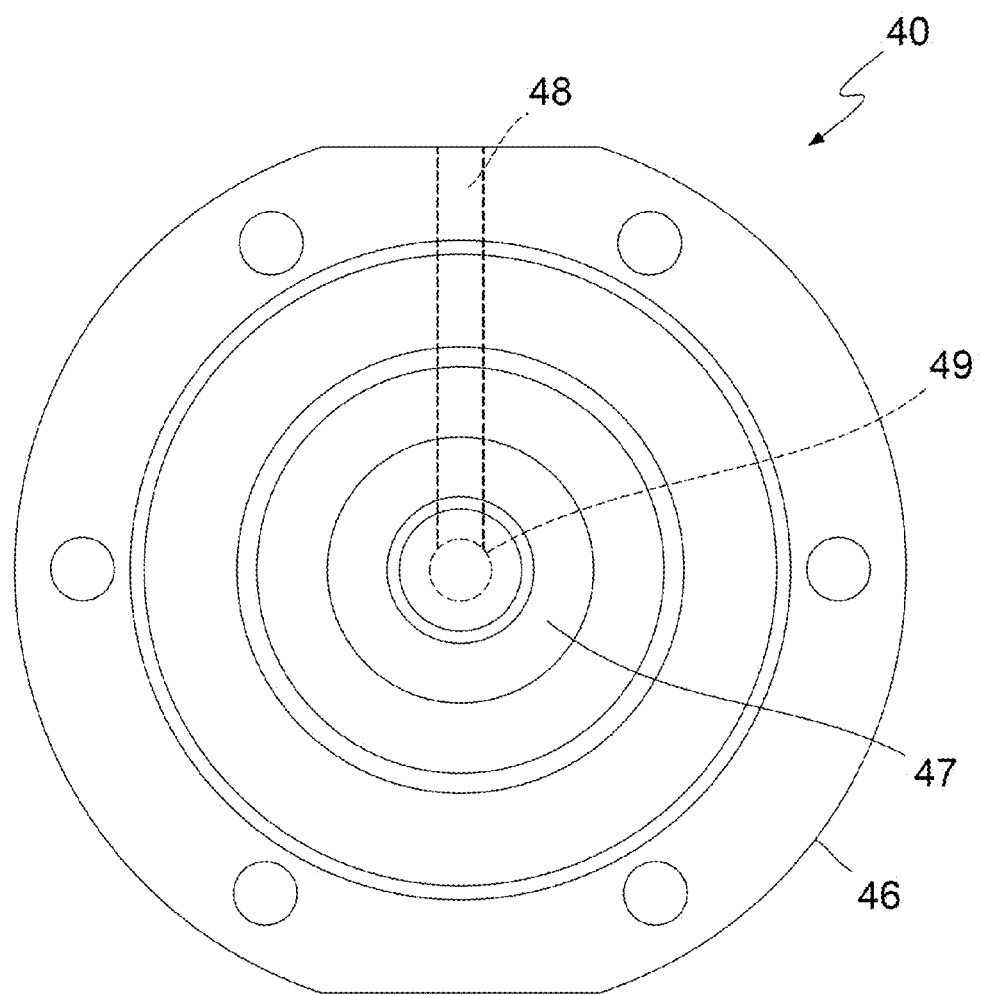
FIG. 4 is a bottom view of an exemplary plunger pin.
Figure 5:
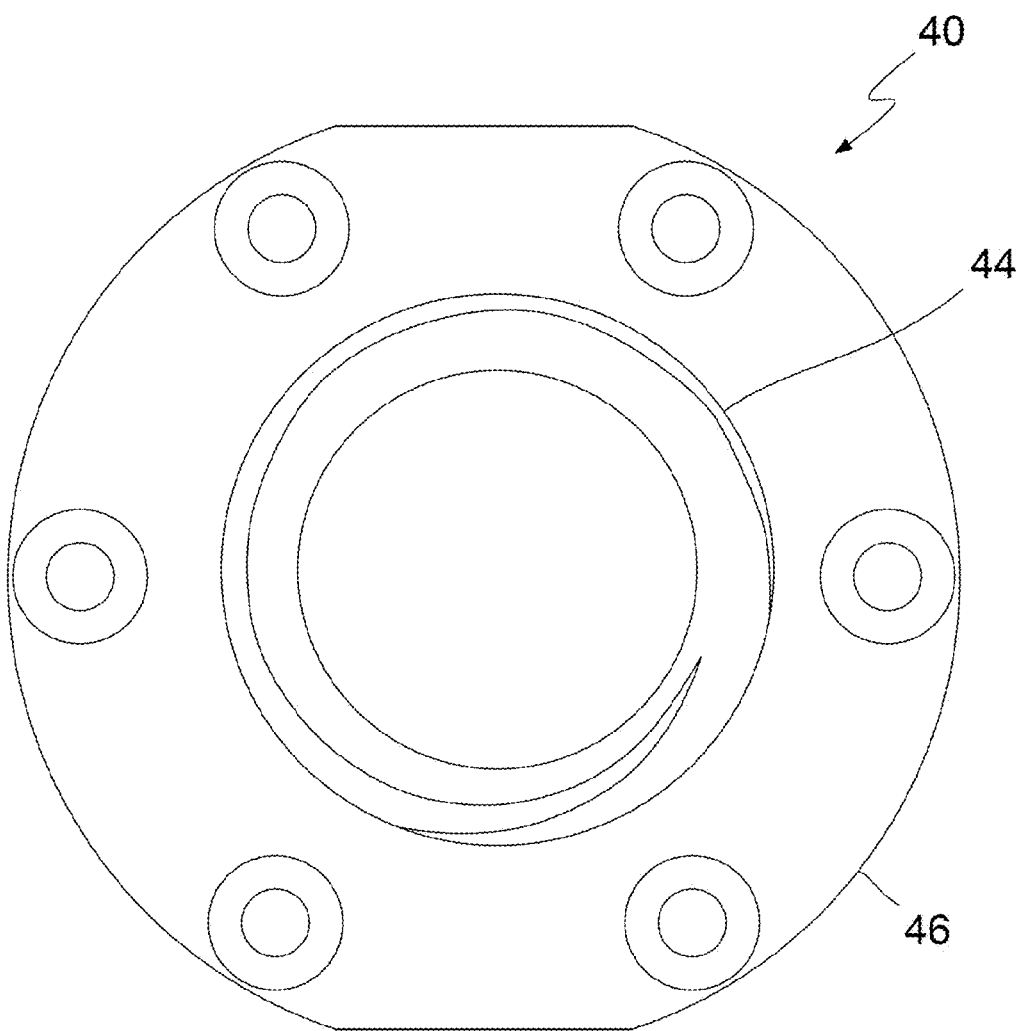
FIG. 5 is a top view of an exemplary plunger pin.
Figure 6:
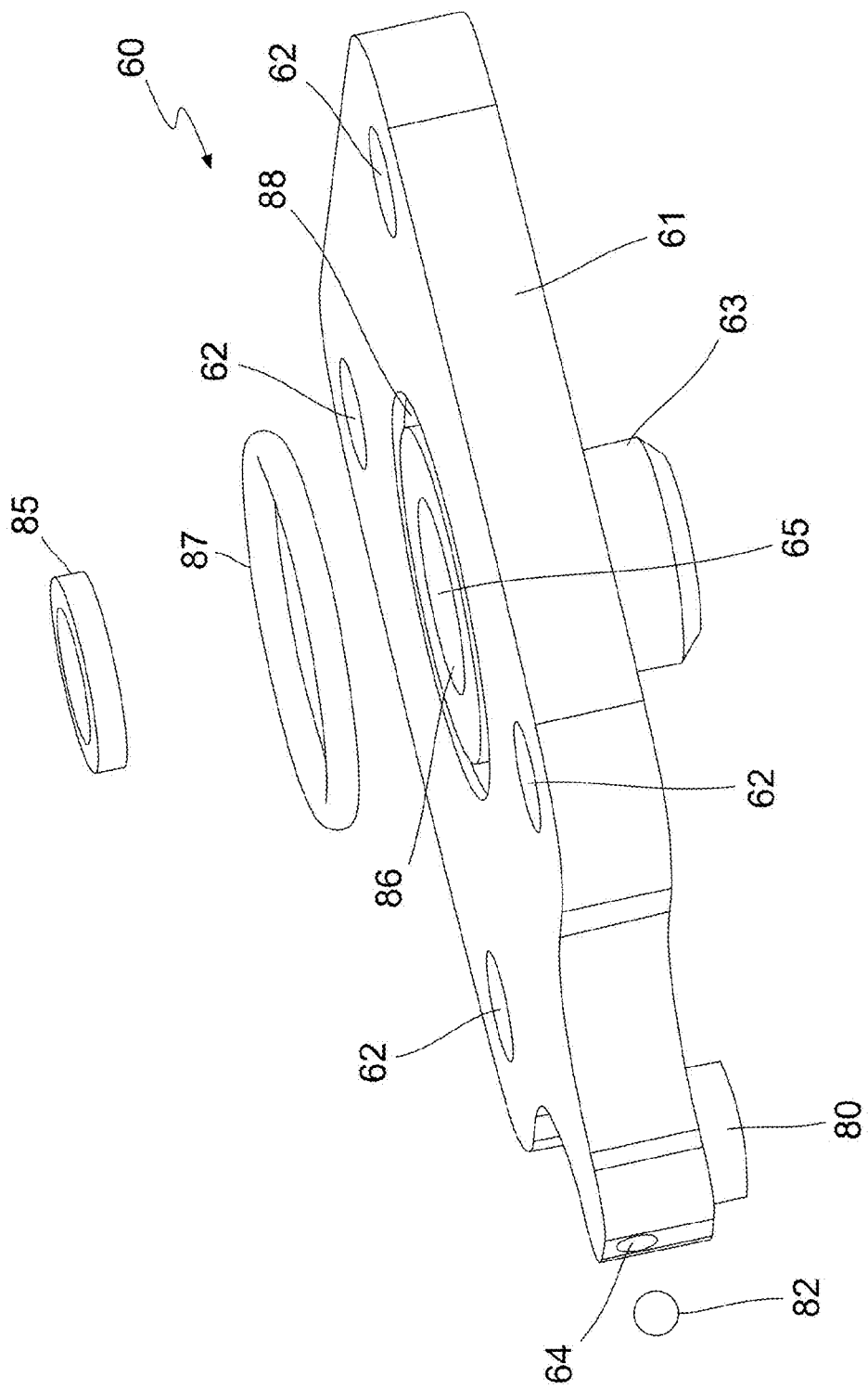
FIG. 6 is an exploded perspective view of an exemplary manifold.
Figure 7:
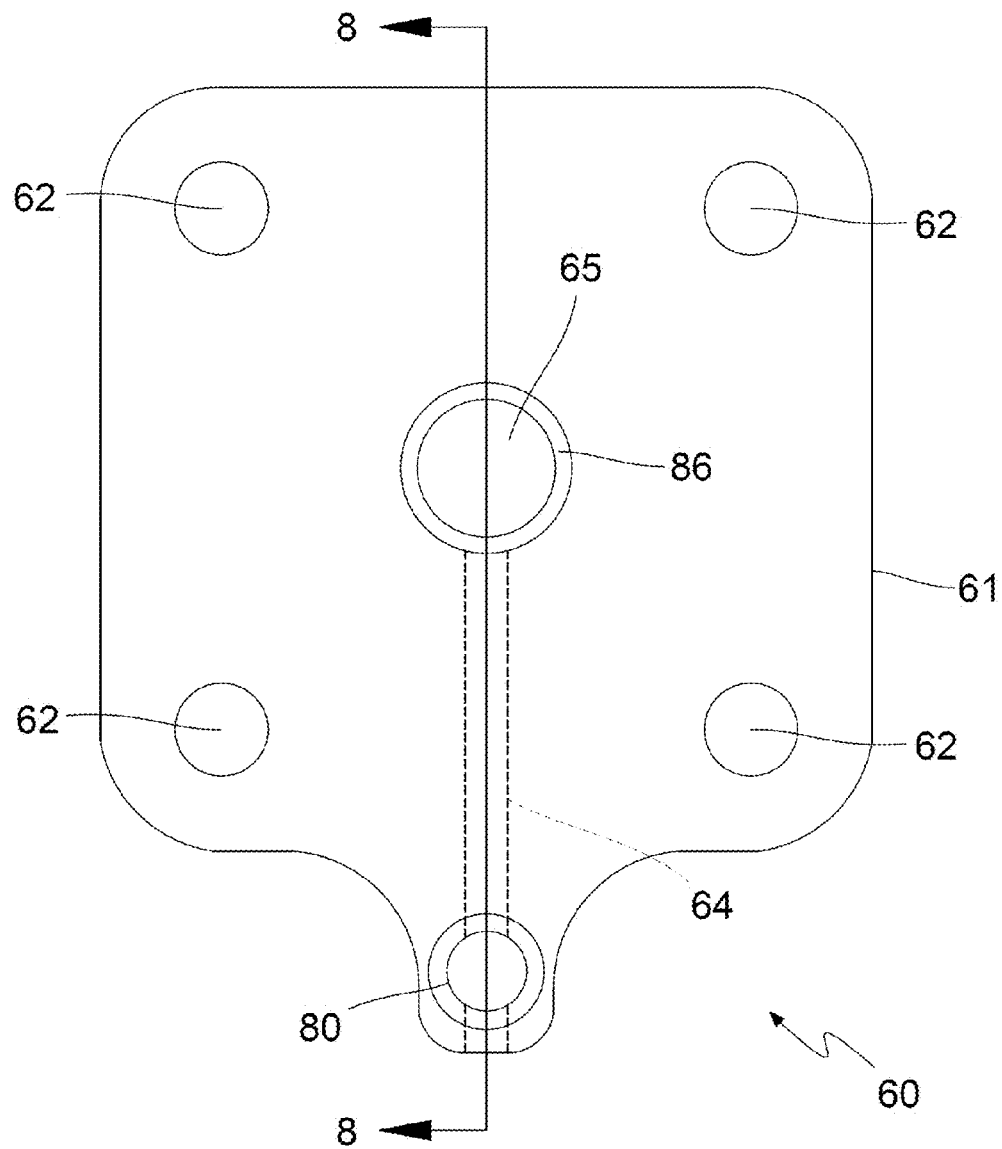
FIG. 7 is a plan view of an exemplary manifold.
Figure 8:
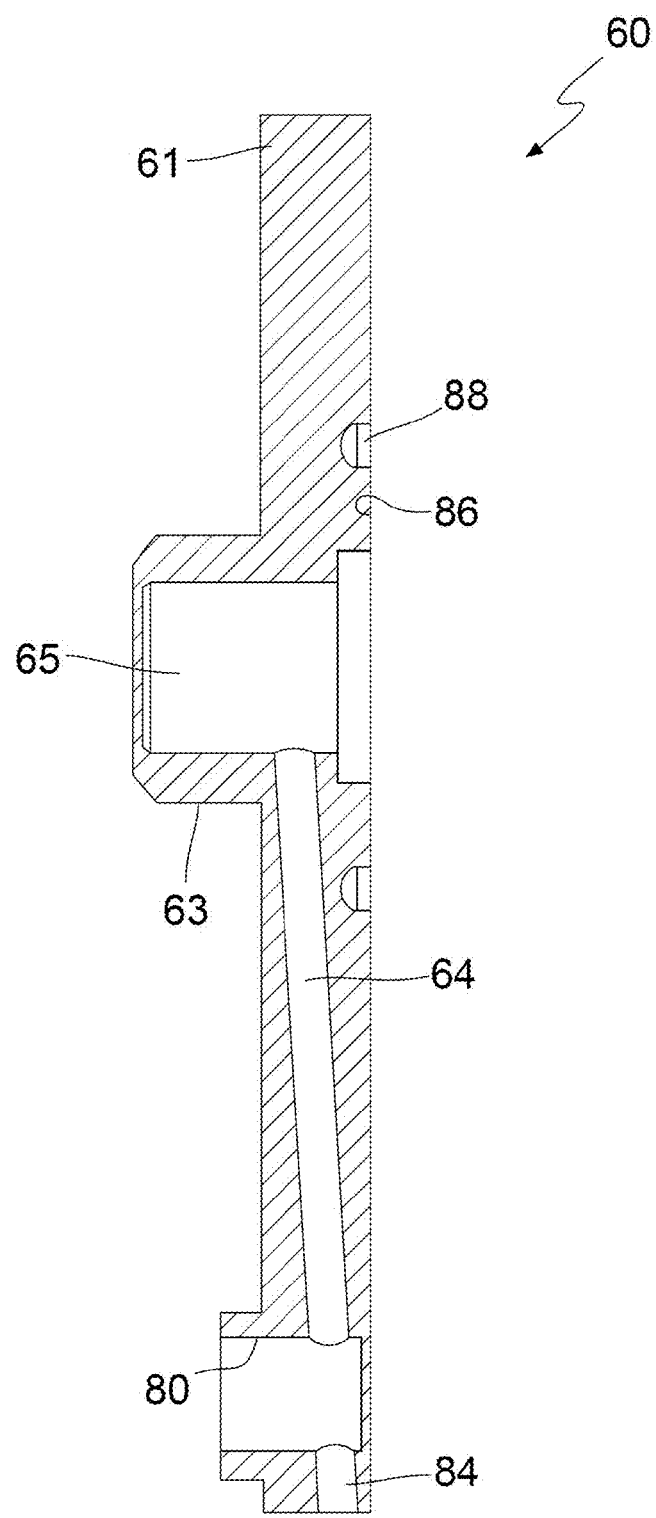
FIG. 8 is a cross-sectional view of an exemplary manifold.
Figure 9:
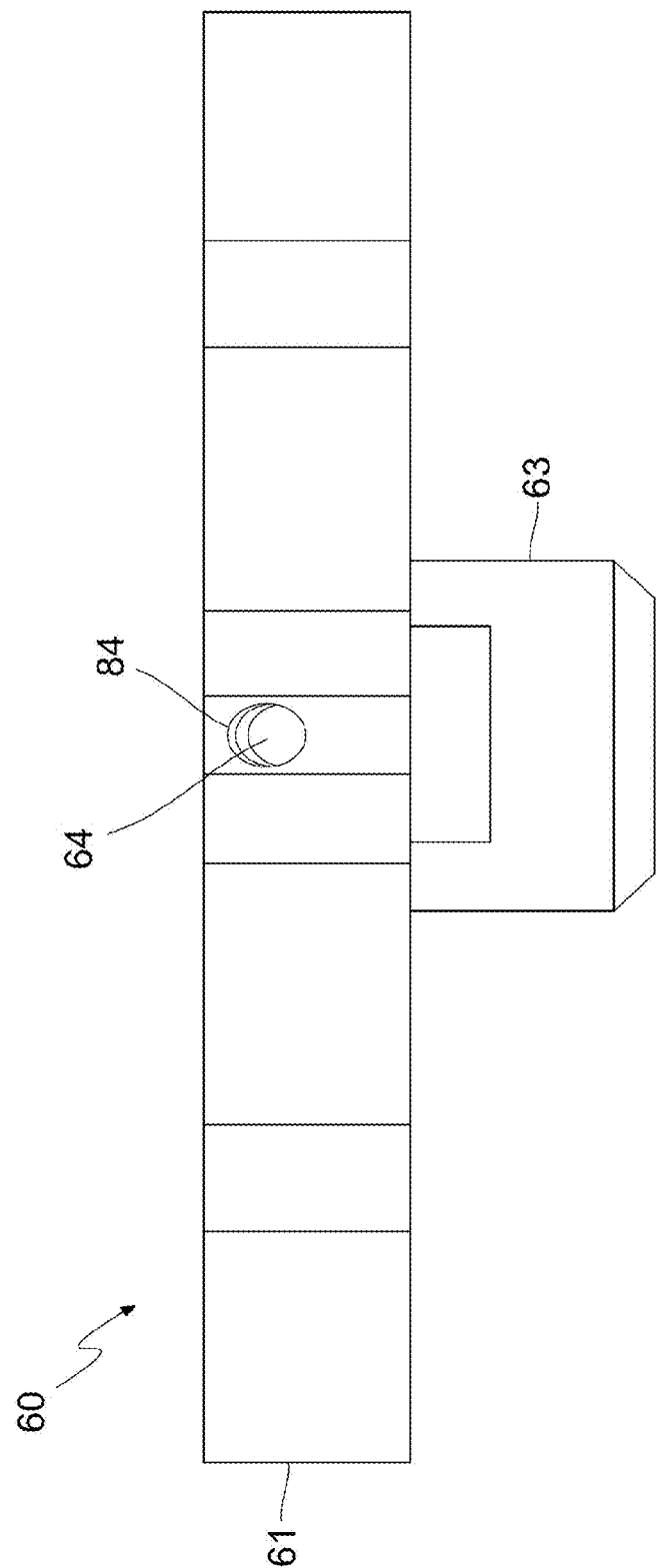
FIG. 9 is an elevation view of an exemplary manifold.

As shown in FIGS. 3 and 4, flange 46 may include a radial passage 48, which may extend generally radially through the flange 46 and which may include a corresponding opening on the diametrically opposite side of flange 46. It is within the scope of the disclosure to incorporate any number of radial passages 48 within the flange 46. Passage 48 may be internally interconnected (in fluid communication) with axial passage 49, which may extend from a distal end 47 of the plunger pin 40 and through the ratchet portion 42.

Exemplary embodiments of the plunger pin 40 may include a gasket 41 (such as an o-ring or a flat washer) which may be seated on an annular surface 45 adjacent to flange 46. Gasket 41 may facilitate a seal between the plunger pin 40 and the locking device 30 as described in greater detail below.

As shown in FIG. 1, when the patient's residual limb 2 and the flexible liner 50 are inserted into the socket 20, the plunger pin 40 may extend through a central hole 33 in the locking device 30, through an opening 29 in the distal end of the socket 20, and into manifold 60 (manifold 60 is depicted in FIGS. 6-9).

Figure 10:
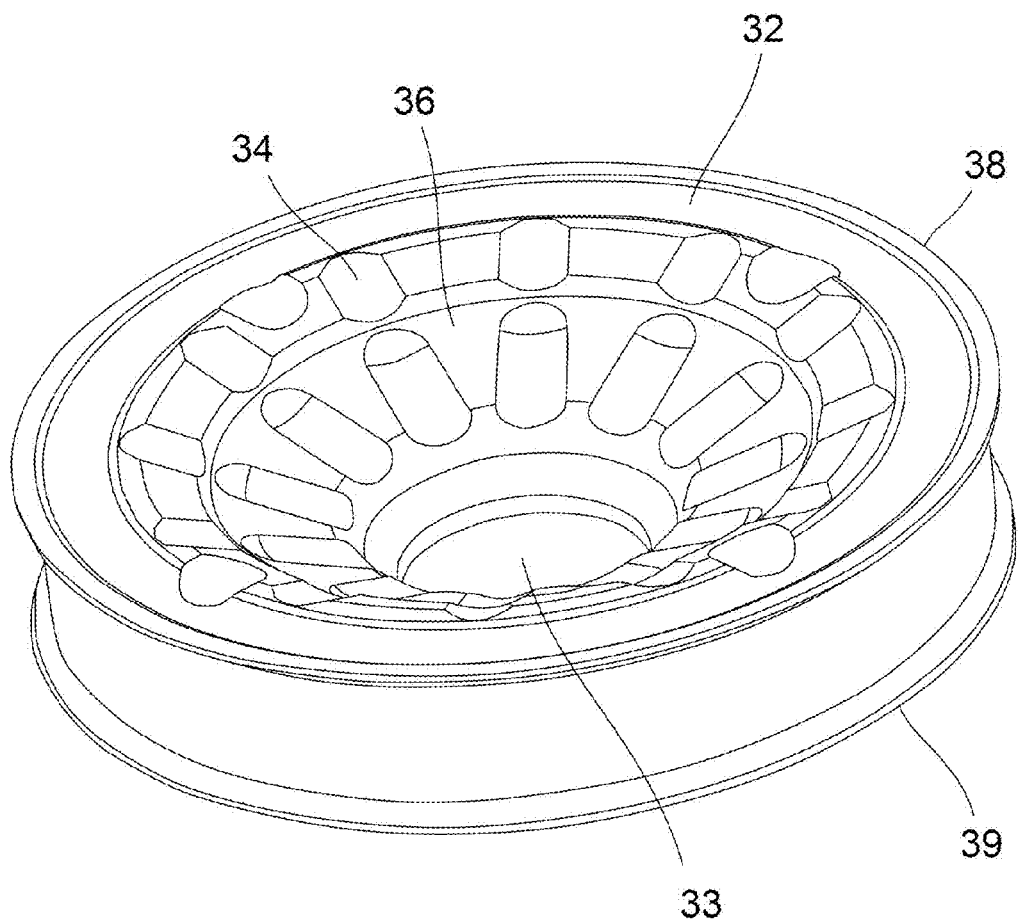
FIG. 10 is a perspective view of an exemplary cushion.
Figure 11:
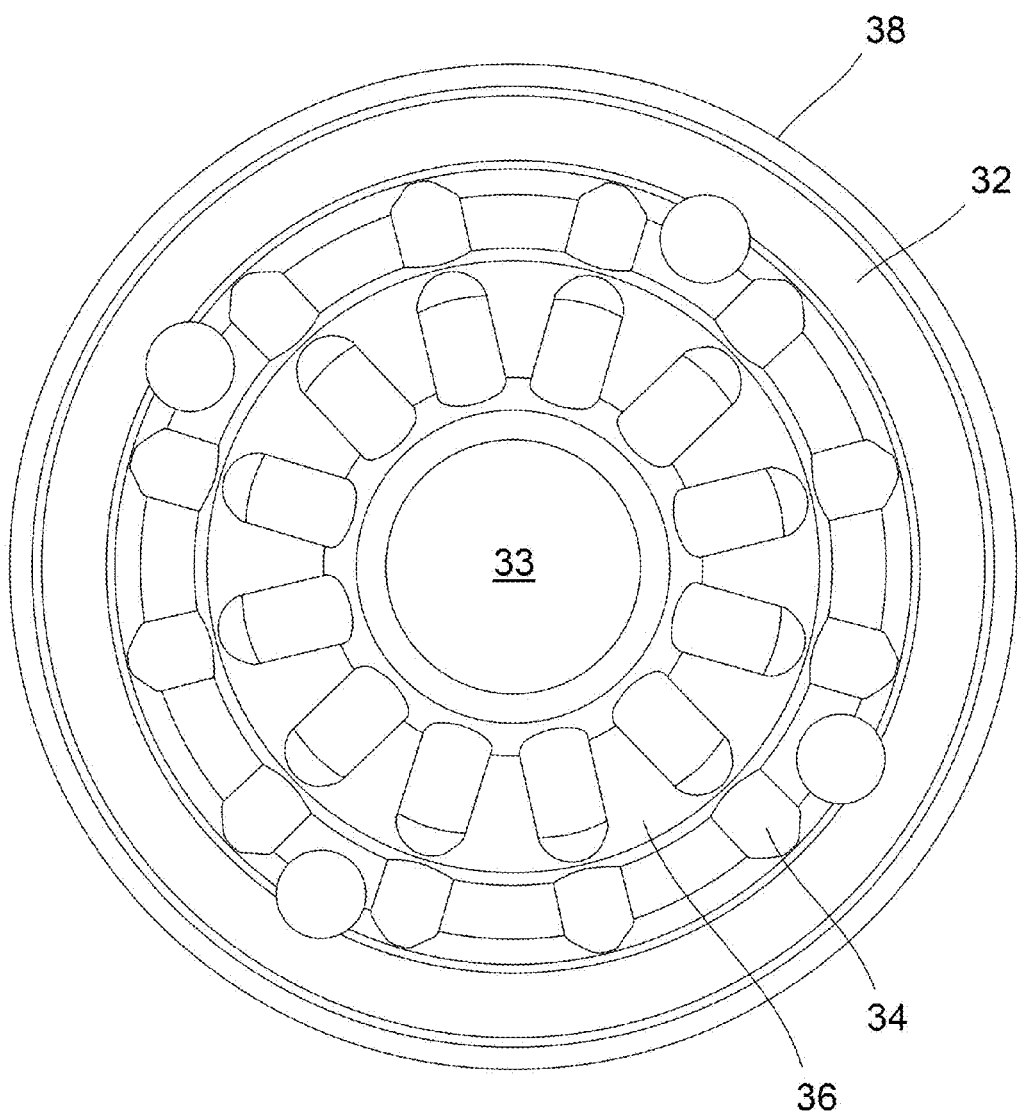
FIG. 11 is a plan view of an exemplary cushion.

Locking device 30, which may include a central hole 33 for receiving the plunger pin 40, may include a lock 31 (such as a shuttle lock sold by Prosthetic Design, Inc. of Clayton, Ohio). The locking device 30 may also include a cushion 32 interposing the liner 50 and the lock 31. As depicted in FIGS. 10-11, cushion 32 may include an aperture 36 (which may be aligned with central hole 33) for receiving the plunger pin 40 as well as one or more guide grooves 34. One or more rims 38, 39 may circumscribe the cushion 32 and may provide a sealing fit between the cushion 32 and the interior of the socket 20. A sealing fit between the cushion 32 and the interior of the socket 20 may be facilitated by a tight engagement of the cushion 32 within the interior of the socket 20, with or without rims 38, 39. The cushion 32 may be constructed from a resilient material, such as urethane.

As depicted in FIGS. 6-9, manifold 60 may include a generally planar portion 61 including one or more mounting holes 62 extending therein for receiving a fastener. Manifold 60 may include a hole 65 sized to receive the distal end of the plunger pin 40. The hole 65 may extend at least partially within a projection 63 extending distally from the planar portion 61 of manifold 60. The planar portion 61 may include a passage 64 extending therethrough, which may extend from a location near the perimeter of the planar portion to the hole 65. Passage 64 may be fluidically connected to a fitting 80 for coupling with a vacuum device 70.

In the exemplary embodiment depicted in FIGS. 6-9, passage 64 may extend outwardly beyond fitting 80. Ball 82 (a ball bearing, for example) may be fitted within the portion of passage 64 exterior to fitting 80 to seal the outward end of passage 64. Accordingly, any air flowing to or from cavity 65 via passage 64 may flow through fitting 80. It is within the scope of the disclosure to utilize other methods of sealing the exterior end of passage 64, such as a threaded plug and/or a plug retained by an adhesive, for example.

Figure 14:
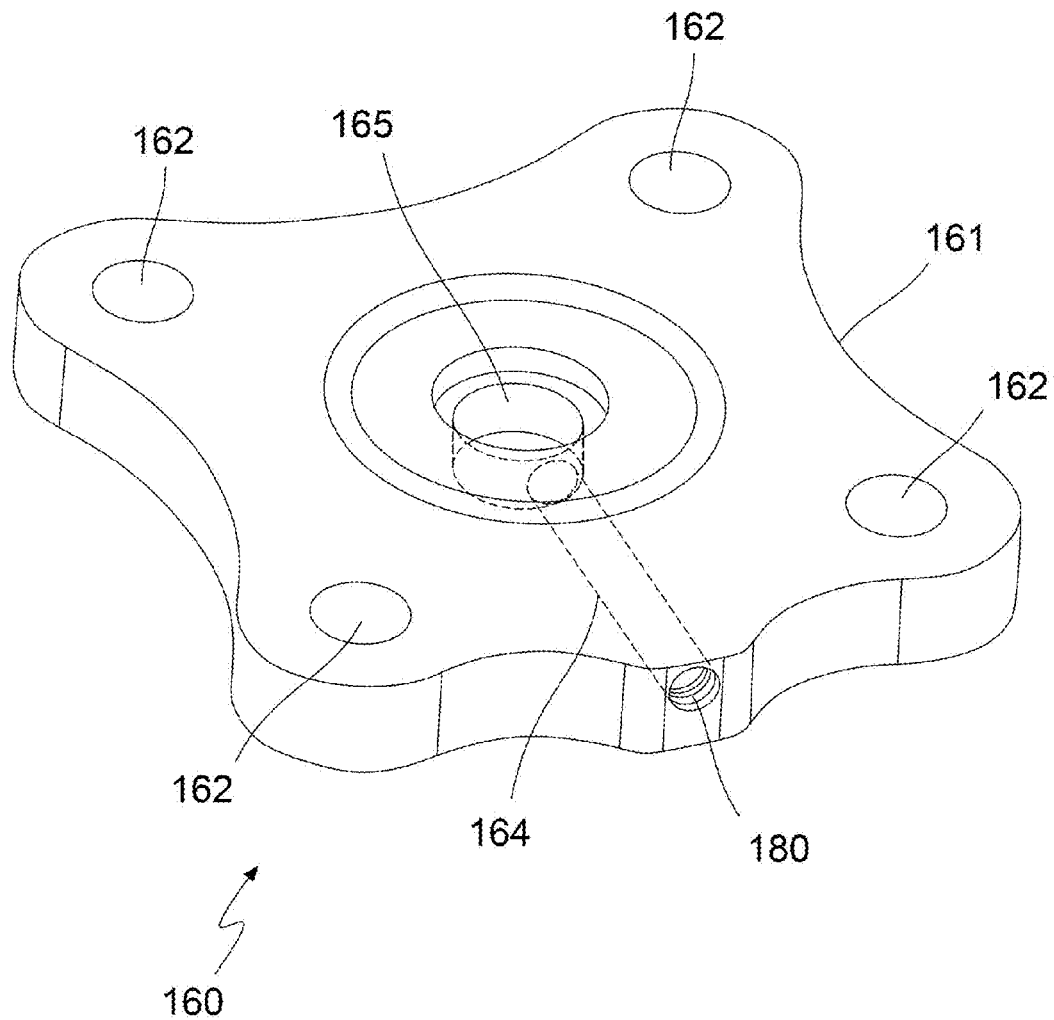
FIG. 14 is a perspective view of an alternative exemplary manifold.

FIG. 14 depicts an alternative exemplary embodiment manifold 160 which may include a hole 165 for receiving the plunger pin 40, mounting holes 162, and a planar portion 161 similar to those described with reference to manifold 60. In this exemplary embodiment, fitting 180 may be located generally in line with passage 164, thus obviating the need to seal an exterior end of passage 64.

Referring back to FIGS. 6-9, a gasket 85 (such as an o-ring or flat washer) may be provided to seal the interface between the hole 65 and the plunger pin 40. In the exemplary manifold 60 shown in FIGS. 6-9, gasket 85 may be mounted within an annular groove 86 on planar portion 61 of manifold 60 and coaxial with the hold 65. Gasket 85 extends radially inward into hole 65 and engages plunger pin 40 when the patient's residual limb 2 and liner 50 are inserted into the socket 20. In particular, gasket 85 may engage surface 90 of plunger pin 40.

A gasket 87 (such as an o-ring or flat washer) may be provided to seal the interface between the exterior distal surface of the socket 20 and the manifold 60. In the exemplary manifold 60 shown in FIGS. 6-9, gasket 87 may be mounted within an annular groove 88 on the proximal surface of planar portion 61 of manifold 60. It is within the scope of the disclosure to provide a similar groove on the distal exterior socket 20 in addition to or in place of groove 88. In addition, exemplary embodiments may include a gasket on the distal surface of the locking mechanism 30 and this gasket may be located within a groove on the locking mechanism 30 and/or the interior of the socket 20.

Vacuum device 70 may comprise any device capable of withdrawing air from within the socket 20. For example, vacuum device 70 may comprise a battery-powered, electrically operated pump. Vacuum device 70 may be mounted on the prosthesis or elsewhere (such as on the patient's body) and may include a mechanism for monitoring and maintaining a desired level of vacuum within the socket. For example, vacuum device 70 may be mounted on an upright assembly of a prosthesis. In an exemplary embodiment, vacuum device 70 may be set to maintain vacuum within the socket at, for example, 20-24 in Hg. The vacuum device 70 may be fluidicly connected to fitting 80 on manifold 60 by, for example, flexible tubing and appropriate fittings. It is within the scope of the disclosure to utilize other vacuum devices, such as a hand-operated vacuum pump.

Figure 12:
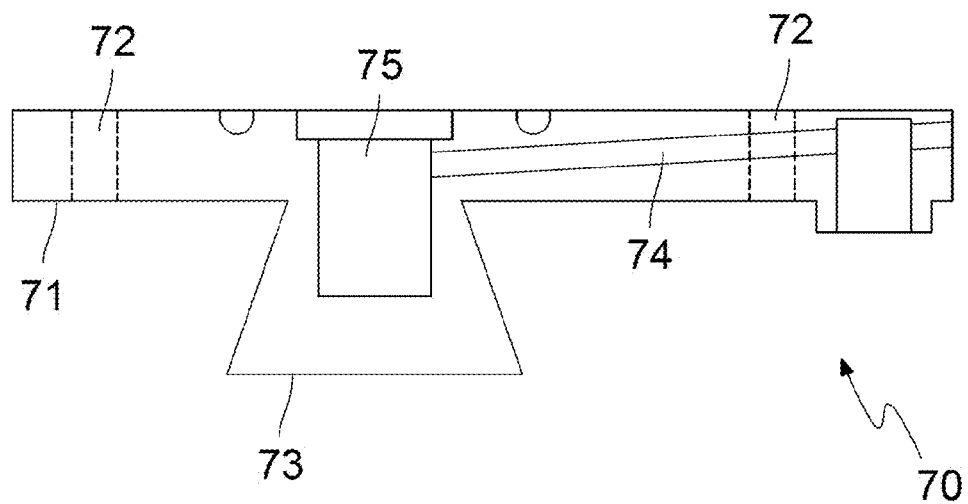
FIG. 12 is a cross-sectional view of an alternative exemplary manifold.

It is within the scope of the disclosure to incorporate a coupling into the manifold adapted to couple to other prosthetic limb components (such as knee components, shin components, and the like). For example, as shown in FIG. 12, an exemplary manifold 70 may include a pyramid 73 for attaching additional components of a prosthesis. Manifold 70 may include a planar portion 71, mounting holes 72, a passage 74, and a hole 75 for receiving the plunger pin, as well as other features generally similar to the corresponding components of manifold 60. A manifold 70 including a pyramid 73 may allow construction of a prosthesis having a smaller overall height than an embodiment having separate manifold and pyramid components. The pyramid 73 may incorporate any known features of pyramids (such as an adjustable lateral position and/or a rotatably adjustable orientation). See, for example, the pyramids sold by Prosthetic Design, Inc. of Clayton, Ohio.

Figure 13:
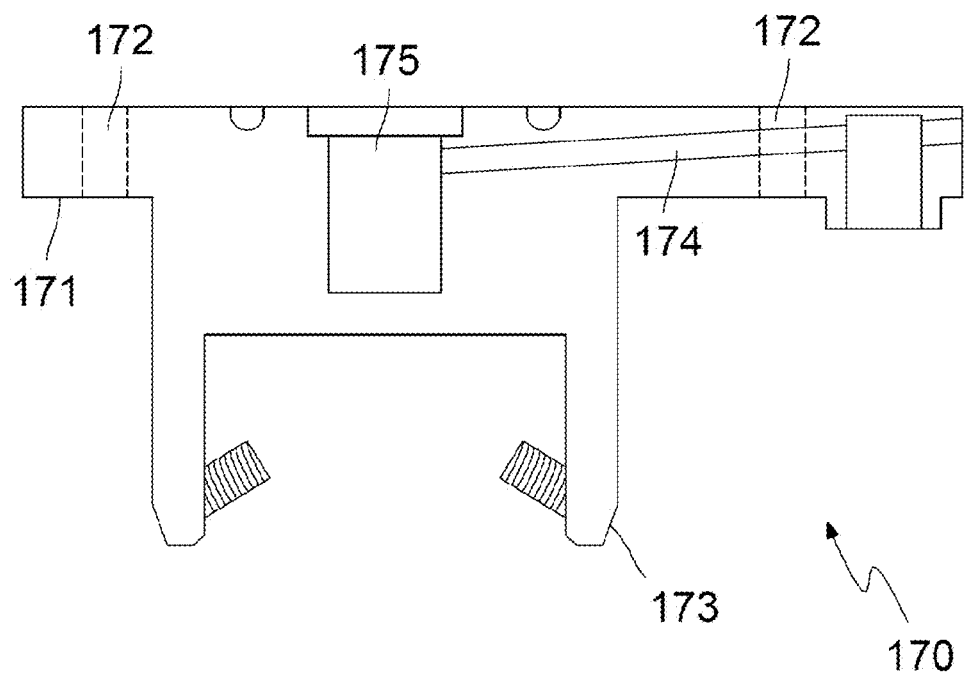
FIG. 13 is a cross sectional view of an alternative exemplary manifold.

FIG. 13 depicts another exemplary manifold 170 which may include a pyramid receiver 173 for attaching additional components of a prosthesis, such as a prosthetic lower leg and foot assembly. Similar to manifold 70 shown in FIG. 12, manifold 170 may include a planar portion 171, mounting holes 172, a passage 174, and a hole 175 for receiving a plunger pin, as well as other features generally similar to the corresponding components of manifold 60. A manifold 170 including a pyramid receiver may allow construction of a prosthesis having a smaller overall height than an embodiment include separate manifold and pyramid components. The pyramid 173 may incorporate any known features of pyramid receivers (such as an adjustable lateral position and/or a rotatably adjustable orientation). See, for example, the pyramid receivers sold by Prosthetic Design, Inc. of Clayton, Ohio. It is within the scope of the disclosure to incorporate any known coupling into the manifold and to use the coupling to attach components of the prosthetic device, for example.

Some exemplary embodiments may be utilized as follows. The amputee may don the flexible liner 50 over her residual limb 2. She may insert the residual limb 2 into the socket 20, allowing the plunger pin 40 to enter the locking mechanism 30. Air displaced by the insertion of the residual limb 2 into the socket 20 may be vented via any gaps present between the liner 50 and the proximal end of the socket 20. Once residual limb 2 is fully inserted into socket 20, flange 46 of plunger pin 40 may compress gasket 41 against a proximal surface of the locking mechanism 30. The amputee may roll a sealing sleeve 99 such that it seals the proximal opening of the socket 20 to the liner 50.

With the residual limb 2 and liner 50 fully inserted into the socket, a sealed volume is created between the exterior surface of the liner 50 and the interior surface 20 of the socket. The proximal end of socket 20 is sealed to liner 50 using, for example, a sealing sleeve 99. The distal end of socket 20 is sealed to the perimeter of cushion 32. Cushion 32 is sealed to locking mechanism 30, which is sealingly engaged with plunger pin 40 by gasket 41. Thus, passages 48, 49 through plunger pin 40 provide the only path for fluidic communication with the sealed volume. In addition, the sealing engagement of gasket 85 with shoulder 90 of plunger pin 40 creates a sealed connection between the sealed volume within the socket and fitting 80. Accordingly, a vacuum applied at fitting 80 draws air from within the sealed volume.

In addition, as discussed above, gasket 87 provides a seal between the exterior distal surface of socket 20 and manifold 60. One or more gaskets or seals may be provided on the latching pin of the locking mechanism 30 to prevent air leakage into central opening 33 of locking mechanism 30 via the internal components of locking mechanism 30. Other locking devices may be sealed in a similar manner using appropriate gaskets or seals. Accordingly, if one or both of gaskets 41, 85 fails, if plunger pin 40 is not fully inserted into locking mechanism 30, or if plunger pin 40 is absent, a sealed connection between the interior of socket 20 and fitting 80 is provided. Specifically, the proximal end of socket 20 is sealed to liner 50 using sealing sleeve 99, the outer circumference of cushion 32 is sealed to the interior of socket 20, cushion 32 is sealed to locking mechanism 30, the latching pin of the locking mechanism 30 is sealed using a gasket, a gasket 100 may provide a seal between the distal surface of the locking mechanism 30 and the interior of the socket 20, and manifold 60 is sealed to the exterior distal end of the socket 20 using gasket 87.

The amputee may operate the vacuum device 70 to withdraw air from within the socket 20. Air within the socket 20 may be withdrawn through passages 48, 49 of the plunger pin 40, hole 65, and passage 64.

To remove the prosthesis, the amputee may turn off the vacuum device 70. The amputee may roll the sealing sleeve 99, thereby providing an air inlet path into the socket 20 via the proximal end of the socket 20. The amputee may withdraw her residual limb 2 from the socket 20 by releasing the locking mechanism 30 (such as by depressing or withdrawing a pin which disengages a latch from the ratchet portion 42 of the plunger pin 40).

An exemplary vacuum device 70 may be adapted to maintain a desired vacuum level within the socket 20, thereby retaining the residual limb 2 within the socket 20. For example, the vacuum device may include one or more pressure sensors and a control circuit that selectively energizes an electrically driven vacuum pump to maintain the desired vacuum level within the socket. This vacuum retention capability may provide advantages known in the art, such as improved comfort and prevention of excessive fluid loss from the residual limb 2.

In the event of a failure of the vacuum device 70 or leakage of air into the socket 20 (or any other cause of loss of vacuum within the socket), the plunger pin 40 and locking mechanism 30 may retain the residual limb 2 within the socket 20. This mechanical backup capability may provide improved safety and reliability, as well as peace of mind for the amputee.

Figure 15:
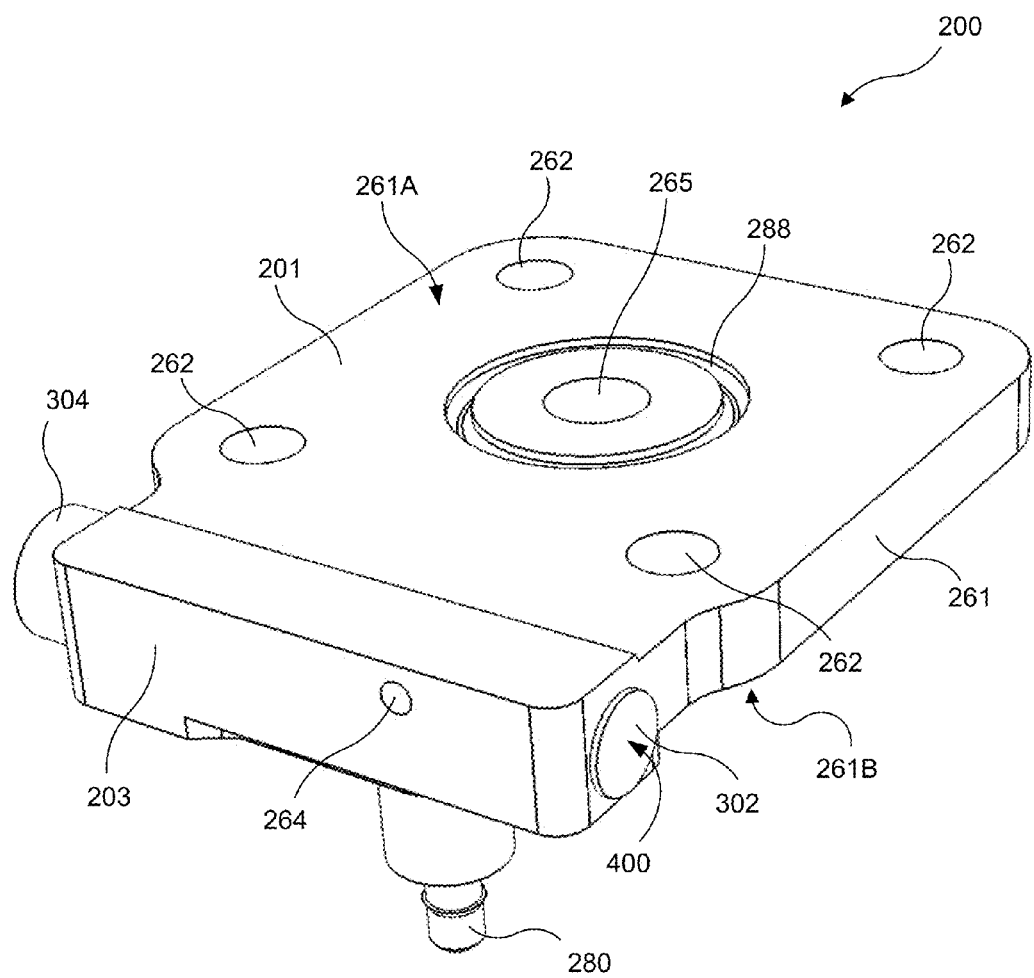
FIG. 15 is a perspective view of a manifold assembly including an integrated spool valve assembly.

FIG. 15 is a perspective view of an example manifold assembly 200 including an integrated spool valve assembly 400. Manifold assembly 200 may include a manifold 201 including an approximately square, generally planar body 261, which may include one or more mounting holes 262 extending therein for receiving a fastener. In some example embodiments, one or more of mounting holes 262 may be through holes. Manifold 201 may include a cavity 265, which may be sized to receive the distal end of plunger pin 40. Cavity 265 may be circumscribed by a groove 288, which may be shaped to receive a gasket (such as an o-ring) therein. Planar body 261 may include a passage 264 extending therethrough, which may extend from the cavity 265 to spool valve assembly 400. Passage 264 may be fluidicly connected to fitting 280, which may be mounted to generally planar body 261 approximate spool valve assembly 400. In some example embodiments, cavity 265 may open to a proximal side 261A of generally planar body 261 and fitting 280 may extend generally distally from a distal side 261B of generally planar body 261. Spool valve assembly 400 may be slidably mounted within a valve housing 203, which may be integrally formed with generally planar body 261, such as approximate an edge of generally planar body 261. For example, planar body 261 and valve housing 203 may comprise a monolithic piece of aluminum. Spool valve assembly 400 may include an open actuator 302 and/or a shut button 304, which may be configured to allow a user to selectively vent cavity 265 via passage 264 as described below.

Figure 16:
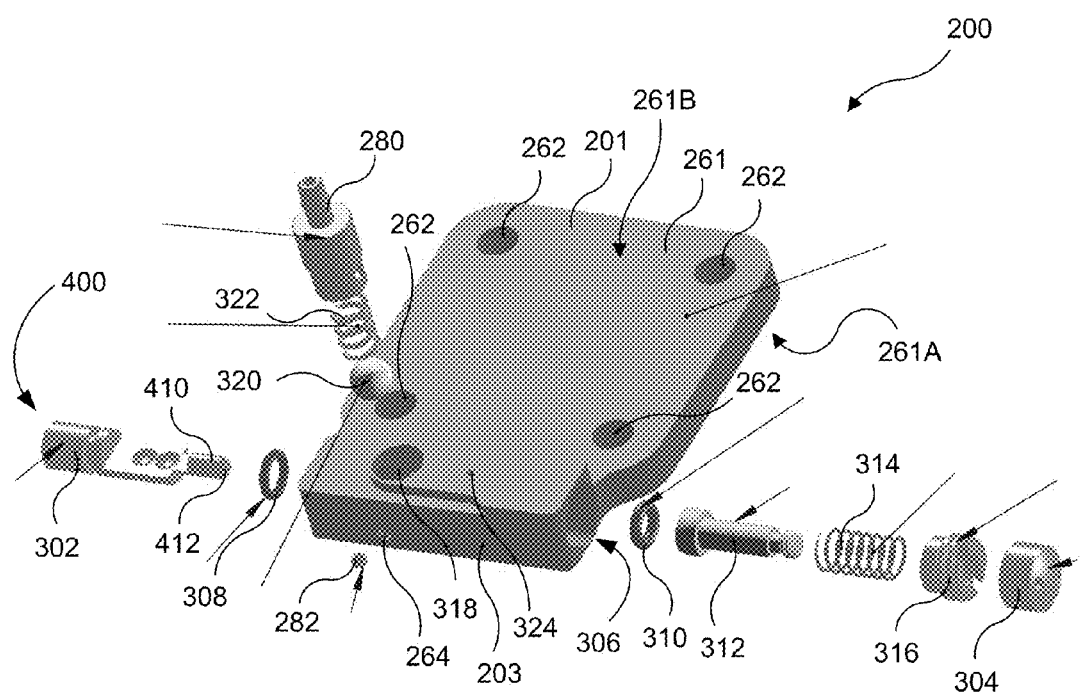
FIG. 16 is an inverted exploded perspective view of a manifold assembly including an integrated spool valve assembly.

FIG. 16 is an inverted exploded perspective view of an example manifold assembly 200 including an integrated spool valve assembly 400. Spool valve assembly 400 may be axially slidably mounted within a generally cylindrical channel 306 provided in valve housing 203 of manifold 201. Valve housing 203 may be located generally along a lateral edge of generally planar body 261 and/or channel 306 may be oriented generally parallel with proximal side 261A and/or distal 261B of generally planar body 261. A vent hole 324 in valve housing 203 may extend into channel 306 to allow venting of passage 264 to the ambient environment when spool valve assembly 400 is in an open position, as discussed below.

In some example embodiments, spool valve assembly 400 may include open actuator 302, which may receive a gasket (such as o-ring 308) to sealingly engage channel 306. Spool valve assembly 400 may include a piston 312, which may selectively seat against a gasket (such as o-ring 310) to selectively vent channel 264 through vent hole 324. Piston 312 may be biased towards o-ring 310 by a spring 314, which may be seated partially within a retainer 316. Piston 312 may extend through retainer 316 to engage shut button 302. When assembled, an end 412 of an extended portion 410 of open actuator 302 may rest against piston 312, thereby allowing open actuator 302 to move piston 312 towards shut button 304 and/or allowing shut button 304 to move open actuator 302 away from shut button 304 (see FIGS. 23 and 24). In some example embodiments, an open end of passage 264 may be plugged, such as by ball bearing 282.

In some example embodiments, fitting 280 may be seated within a generally cylindrical opening 318, which may extend through valve housing 203 into channel 306. Fitting 280 may house a spring 322 arranged to bias a ball 320 towards channel 306, where ball 320 may engage open actuator 302 to latch spool valve assembly 400 in open and/or shut positions as described below. In some example embodiments, fitting 280 may extend generally orthogonally relative to distal side 261B.

Figure 17:
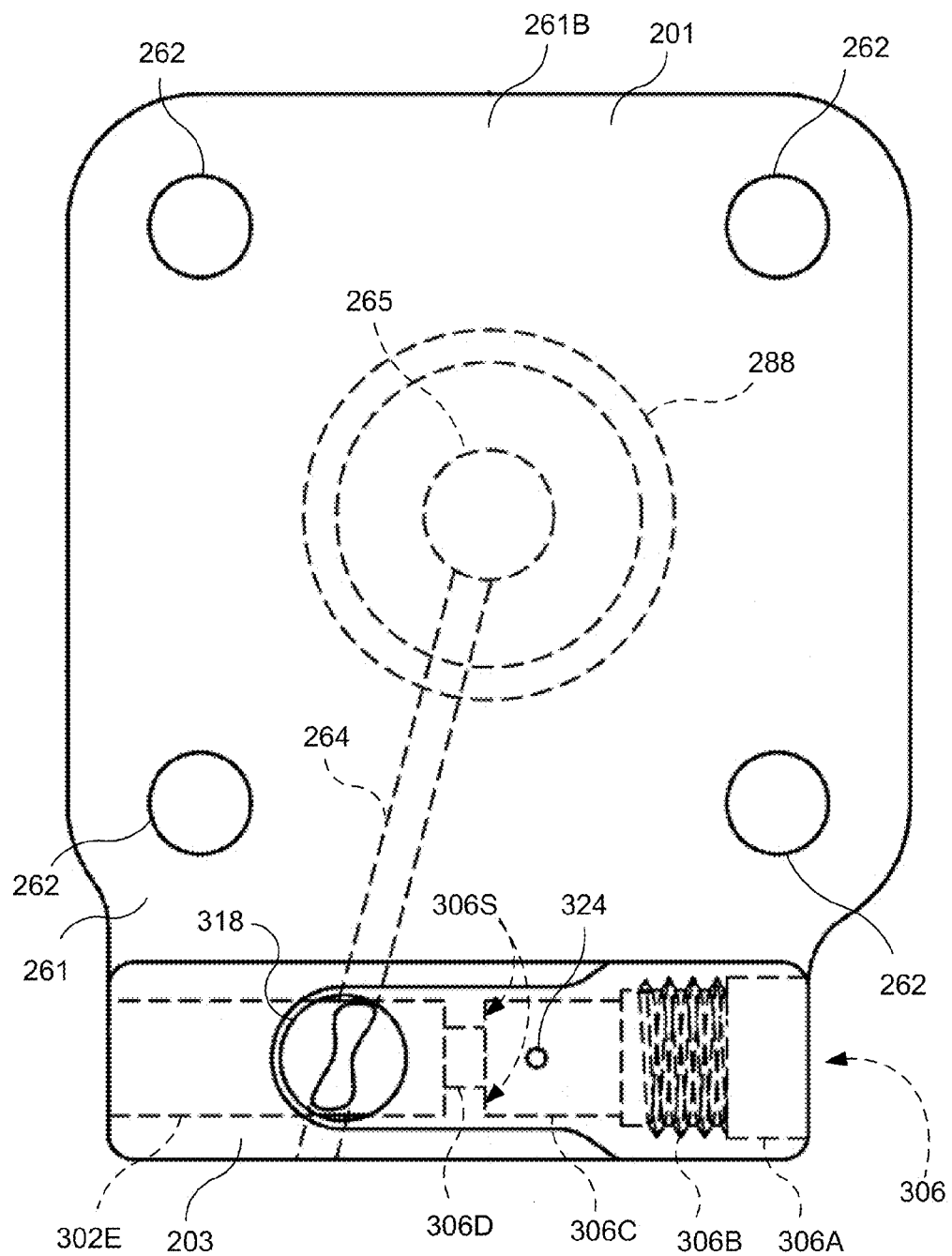
FIG. 17 is a bottom view of a manifold including an integral valve housing.

FIG. 17 is a bottom view of an example manifold 201 including an integral valve housing 203. Channel 306 may include a first section 306A, which may slidably receive shut button 304. Inward from first section 306A, channel 306 may include a second, threaded section 306B, which may threadedly receive retainer 316. Next, channel 306 may included a third section 306C, which may slidably receive piston 312 therein. Vent hole 324 may extend to third section 306C. Next, channel 306 may include a fourth, narrow section 306D. Due to a difference in diameter between third section 306C and fourth, narrow section 306D, a shoulder 306S may be provided at the inner end of third section 306C. Following fourth, narrow section 306D, channel 306 may include a fifth section 306E, which may slidably receive open actuator 302. Passage 264 may extend generally radially from cavity 265 to valve housing 203, such that passage 264 intersects with and fluidicly connects to channel 306 in fifth section 306E. Also, in some example embodiments, cylindrical opening 318 (which may seat fitting 280) may open into fifth section 306E.

Figure 18:
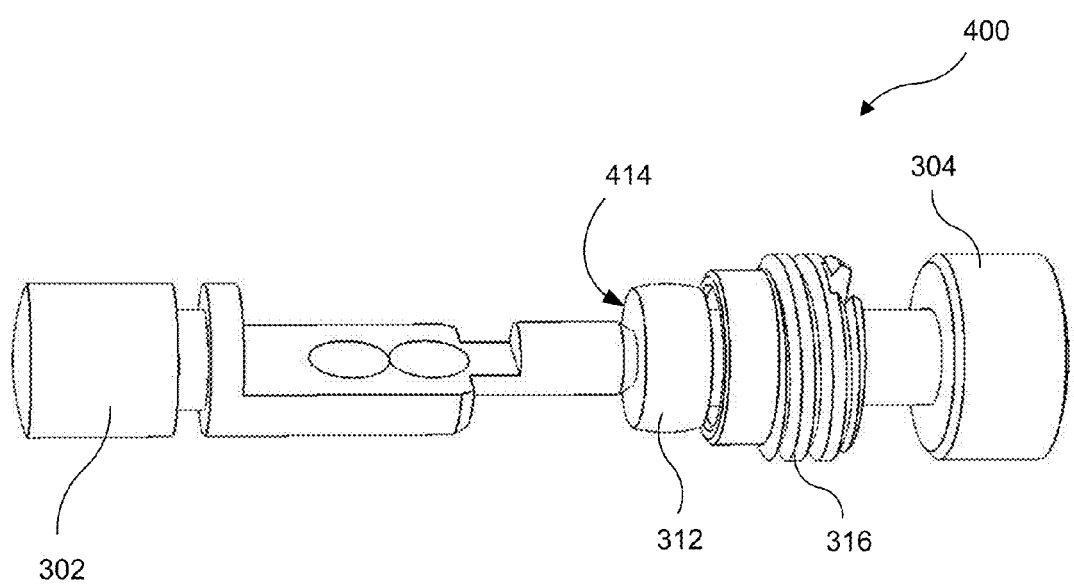
FIG. 18 is a perspective view of a spool valve assembly.

FIG. 18 is a perspective view of an example spool valve assembly 400, which may include open actuator 302, piston 312 (including face 414), retainer 316, and shut button 304.

Figure 19:
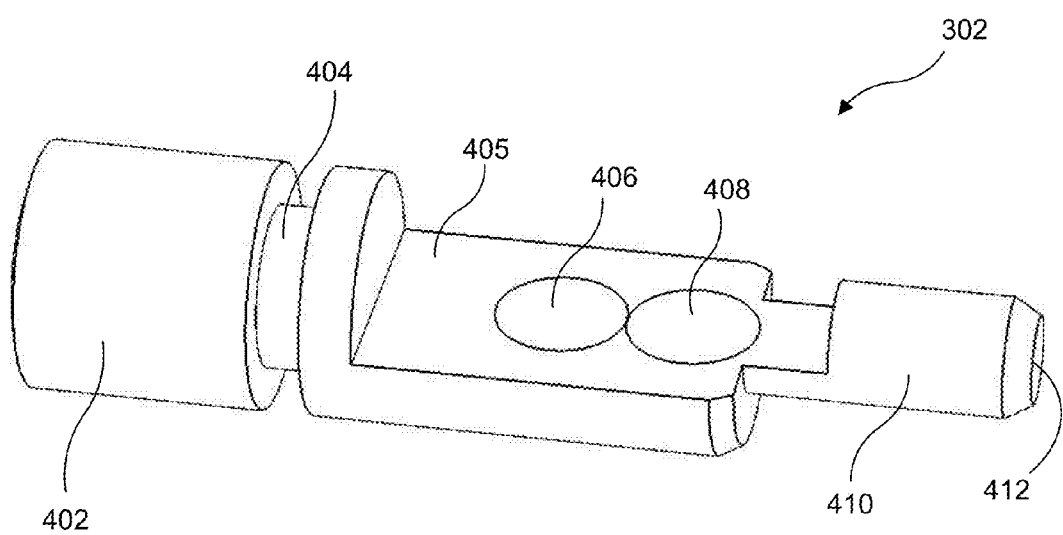
FIG. 19 is a perspective view of a open actuator for a spool valve assembly.
Figure 23:
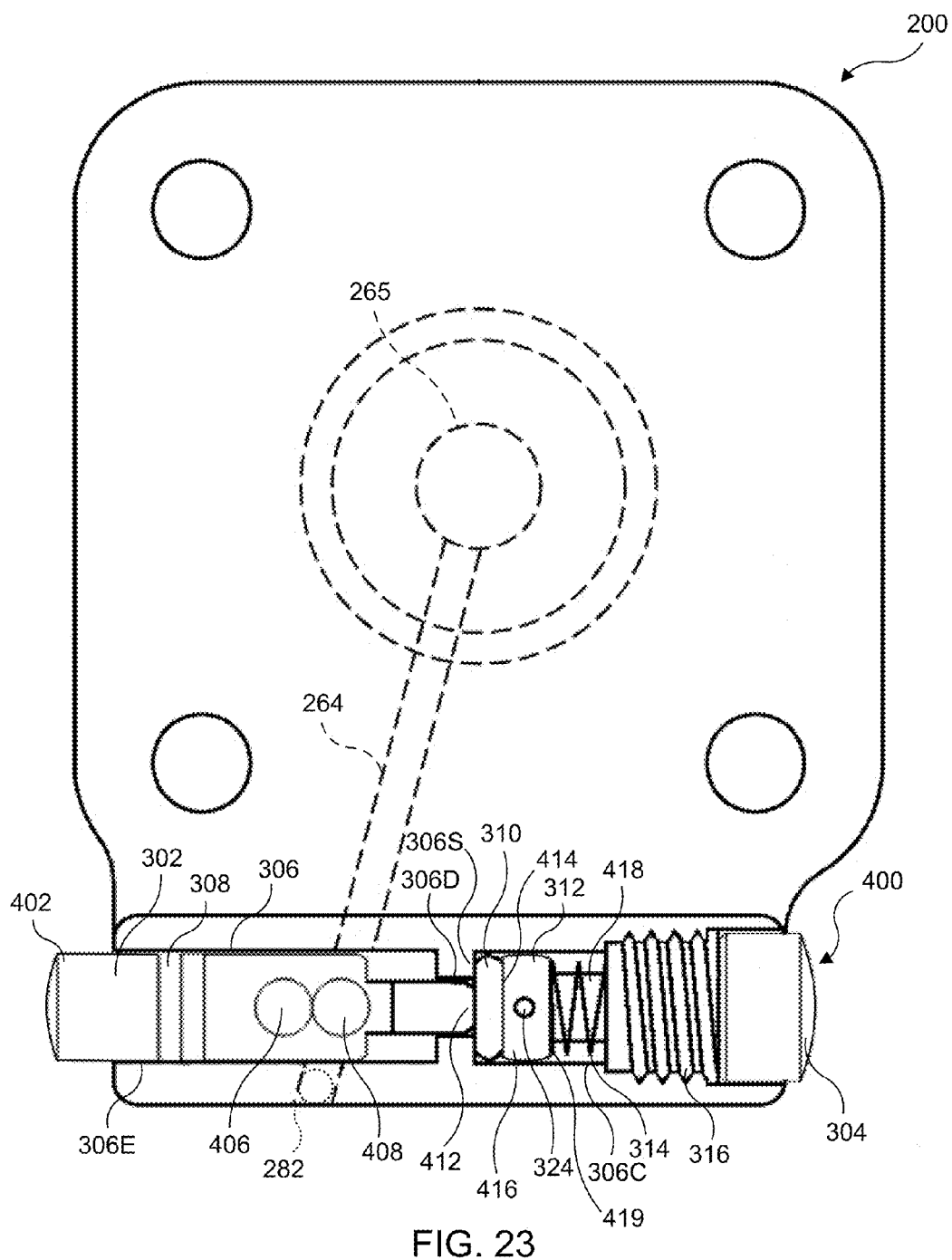
FIG. 23 is a partial cutaway view of a manifold assembly including a spool valve assembly in a shut position.
Figure 24:
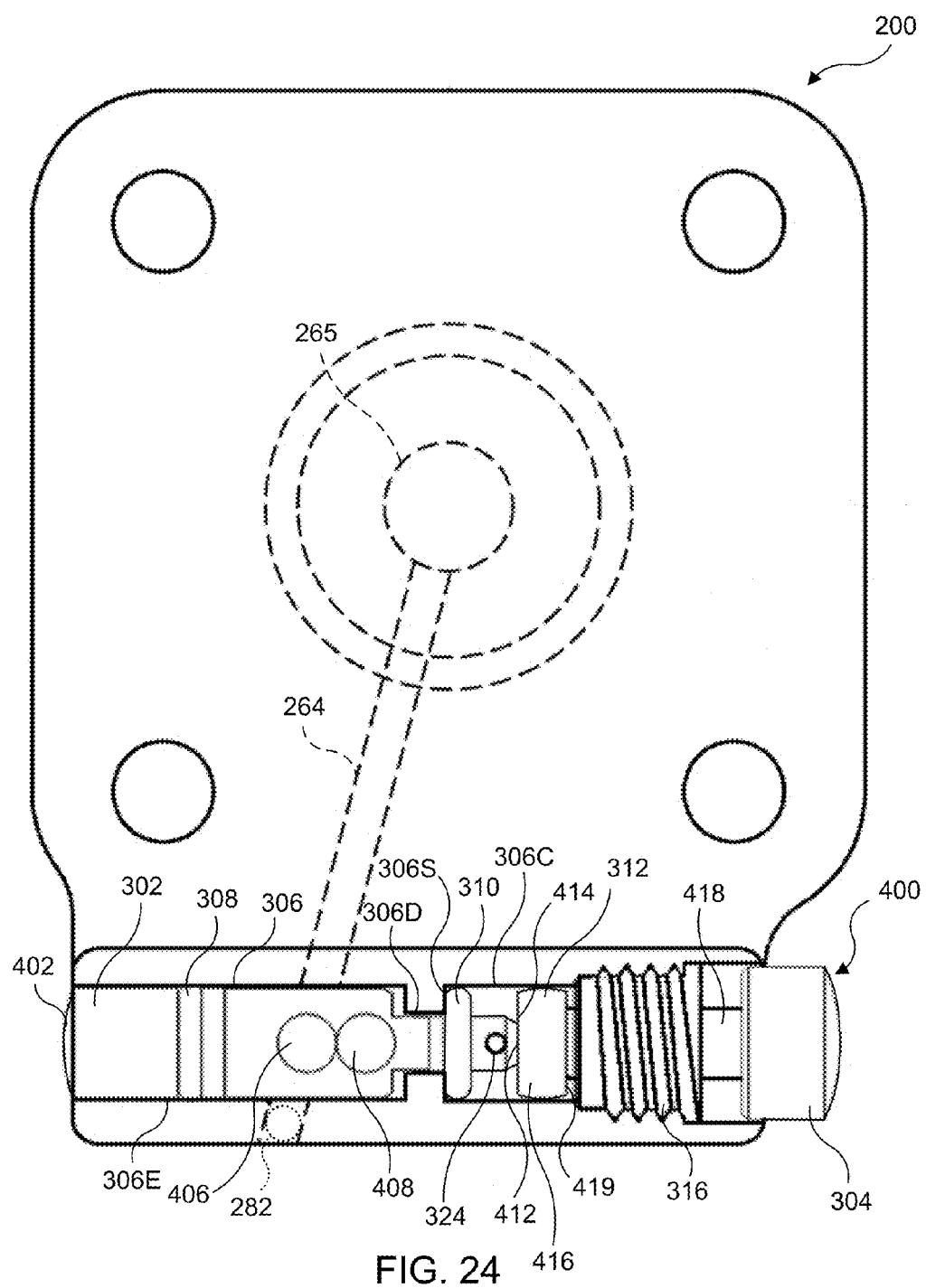
FIG. 24 is a partial cutaway view of a manifold assembly including a spool valve assembly in an open position.

FIG. 19 is a perspective view of an example open actuator 302 for a spool valve assembly 400. Open actuator 302 may include an open button 402 which may extend out of channel 306 to allow a user to shift spool valve assembly 400 from a shut position (e.g., in which cavity 265 is isolated from vent hole 324 as illustrated in FIG. 23) to an open or vent position (e.g., in which cavity 265 is fluidicly connected to vent hole 324 as illustrated in FIG. 24). Adjacent open button 402 may be a coaxial, circumferential groove 404, which may receive o-ring 308 to provide a sealed, sliding interface between open actuator 302 and fifth section 306E of channel 306. Next, open actuator 302 may include a substantially flat distal surface 405 extending in an axial direction from open button 402 which may include first detent 406 and/or second detent 408, which may be sized to engage biased ball 320 (see FIG. 16). In the open position, ball 320 may be biased to engage detent 406. In the shut position, ball 320 may be biased to engage detent 408. The engagement between ball 320 and detents 406, 408 may be sufficient to prevent movement of spool valve assembly 400 absent an externally applied force. Axially beyond distal flat surface 405, open actuator 302 may include a coaxial, cylindrical extension 410, which may be sized to extend through fourth, narrow section 306D of channel 306 (see FIGS. 23 and 24). An end 412 of extension 410 may rest against piston 312 when spool valve assembly 400 is assembled (see FIGS. 18, 23, and 24).

Figure 20:
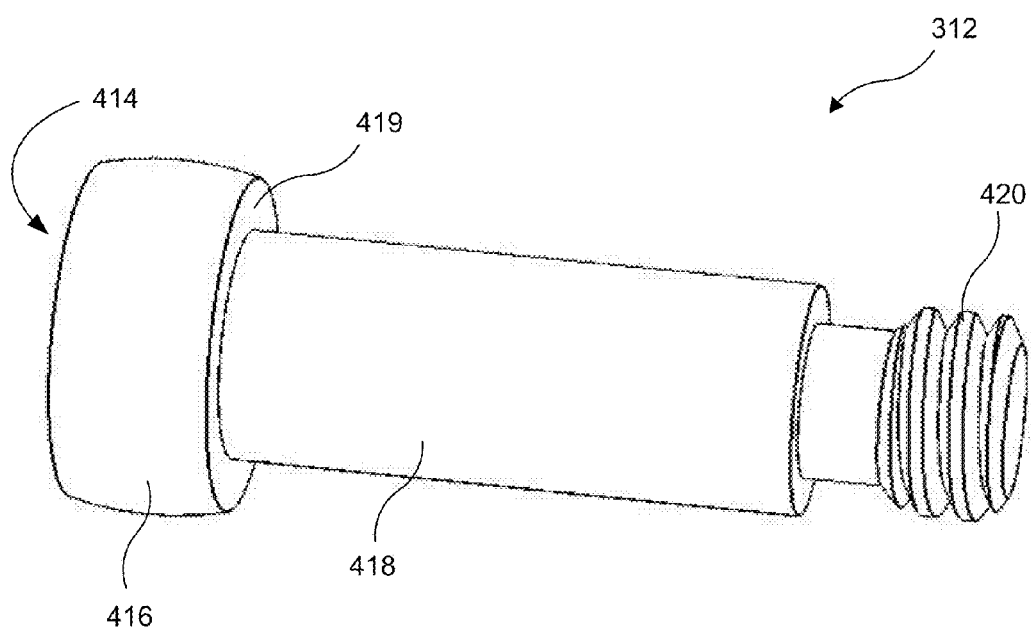
FIG. 20 is a perspective view of a piston for a spool valve assembly.

FIG. 20 is a perspective view of an example piston 312 for a spool valve assembly 400. Piston 312 may include a face 414, which may be provided on an end of a widened cylindrical portion 416 and which may contact end 412 of open actuator 302 (see FIGS. 18, 23, and 24). Shaft 418 may extend axially from widened portion 416 and may include a threaded section 420 at an opposite end thereof. Shaft 418 may be sized to slidably extend through retainer 316 and to receive spring 314 thereabout. One end of spring 314 may press against a shoulder 419 formed by a difference in diameter between shaft 418 and widened section 416. Threaded section 420 may be configured to threadedly engage shut button 304 (see FIGS. 18, 23, and 24).

Figure 21:
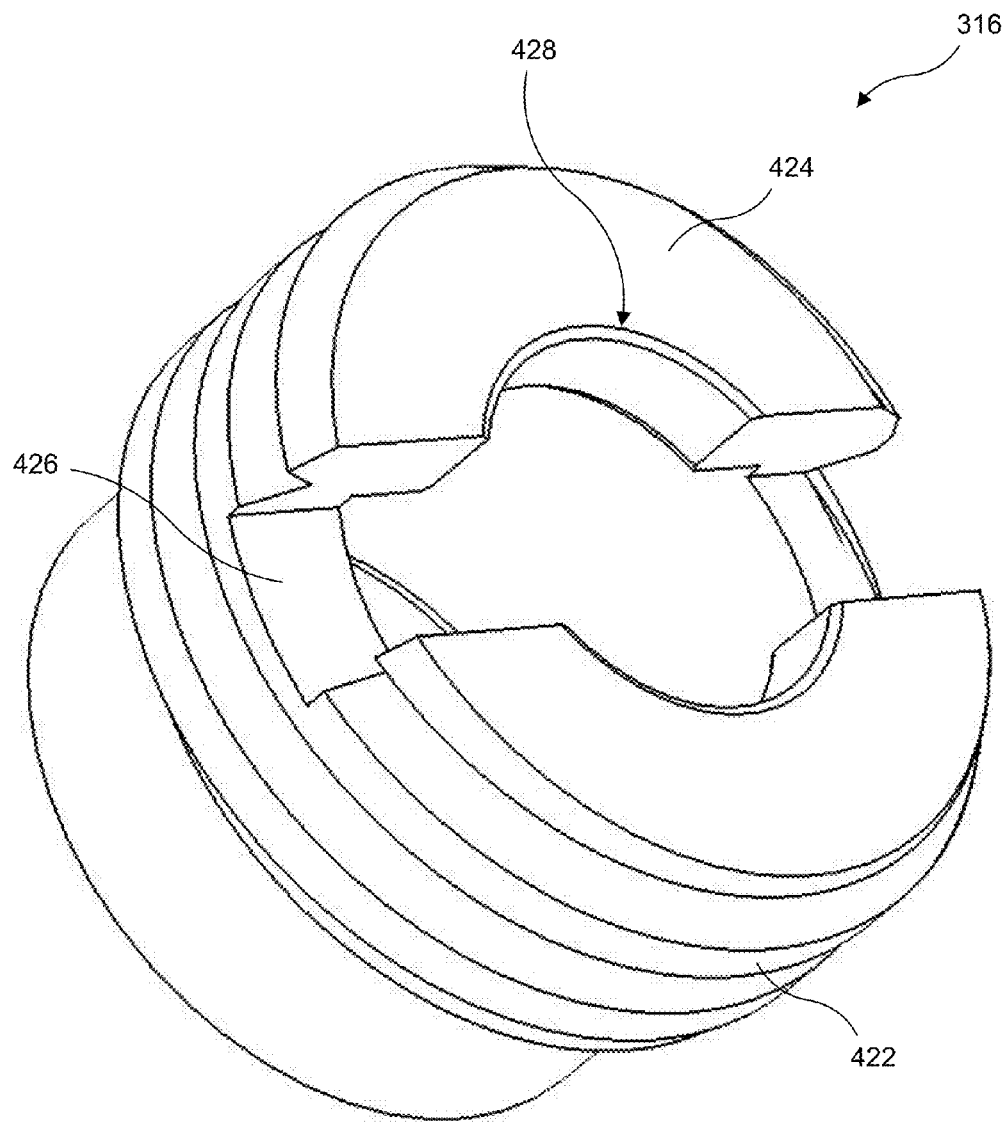
FIG. 21 is a perspective view of a retainer for a spool valve assembly.

FIG. 21 is a perspective view of an example retainer 316 for a spool valve assembly 400. Retainer 316 may include a hollow, generally cylindrical body which may include a threaded section 422 on its outer surface. Threaded section 422 of retainer 316 may be configured to threadedly engage second, threaded section 306B of channel 306 (see FIG. 17). One end of retainer 316 may include a radially inwardly extending circumferential flange 424, which may include a central opening 428 for receiving shaft 418 of piston 312 therethrough (see FIGS. 18, 23, 24). Flange 424 may engage spring 314 such that spring 314 may be captured between flange 424 and shoulder 419 of piston 312, thereby biasing flange 419 of piston 312 away from flange 424 (see FIG. 23). Flange 424 may include a diametric slot 426, which may be engaged by a tool during installation of retainer 316 in channel 306.

Figure 22:
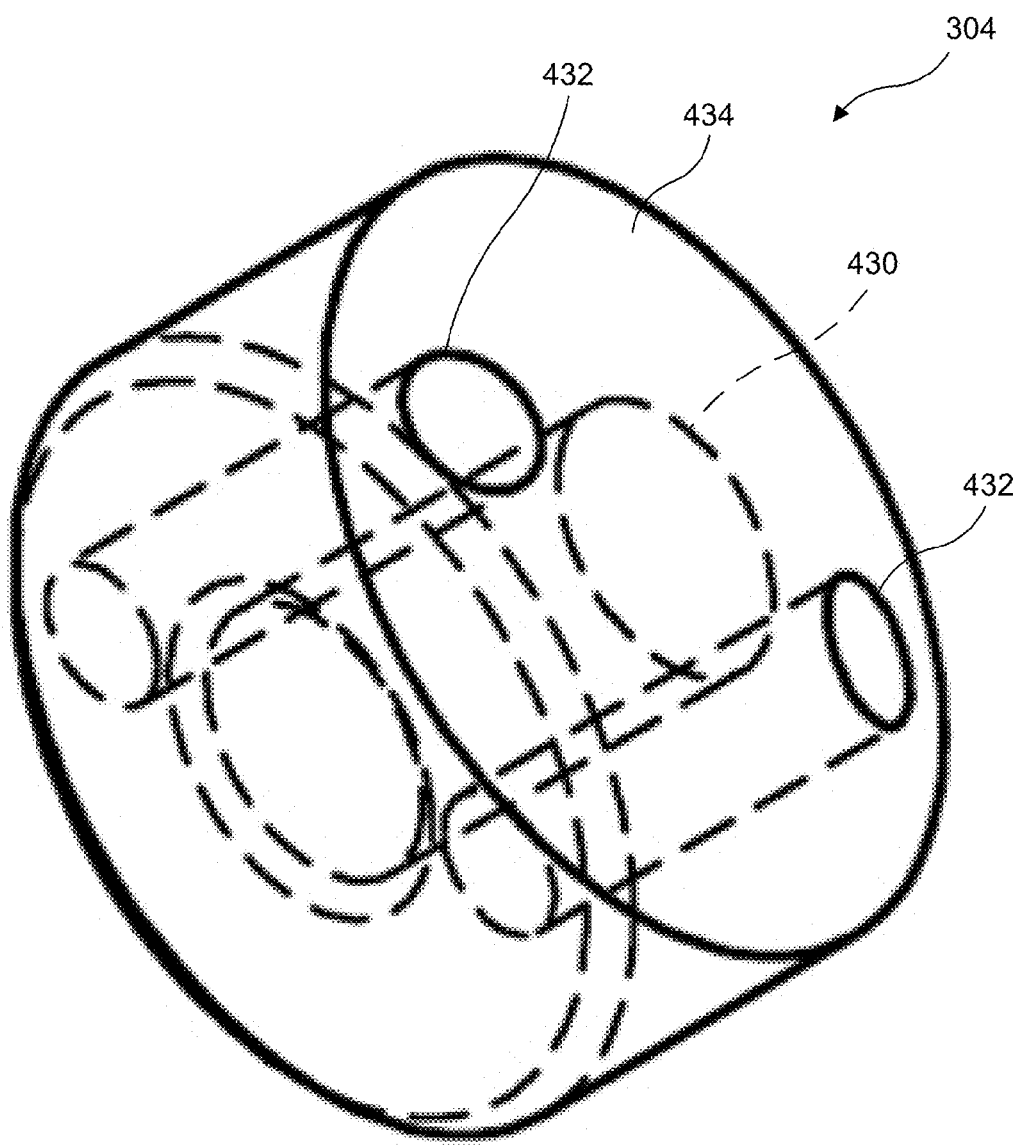
FIG. 22 is a perspective view of a shut button for a spool valve assembly.

FIG. 22 is a perspective view of an example shut button 304 for a spool valve assembly 400. Shut button 304 may include a central opening 430, which may be internally threaded, for coupling with threaded section 420 of piston 312 (see FIGS. 18, 23, and 24). One or more axial through holes 432 may be arranged to allow a tool to reach slot 426 of retainer 316 during installation of spool valve assembly into channel 306 (see FIGS. 23 and 24). An end face 434 may face outwardly from channel 306 to allow a user to operate shut button 304.

Referring to FIG. 23, some example manifold assemblies 200 including integrated spool valve assemblies 400 as illustrated in FIGS. 15-22 may be placed in a shut position in which detent 408 of open actuator 302 may be engaged by ball 320 (see FIG. 16) and open button 402 may extend outwardly from fifth section 306E. End 412 of open actuator 302 may be withdrawn into fourth, narrow section 306D of channel 306, thereby allowing the biasing force of spring 314 to press face 414 of piston towards shoulder 306S. O-ring 310 may be compressed between face 414 of piston and shoulder 306S, thereby providing a sealed interface between piston 312 and shoulder 306S. In this shut position, cavity 265 may be fluidically connected to fitting 280 (see FIG. 16) via passage 264, fifth section 306E, and opening 318 (see FIG. 16). This fluid path may be sealed from the environment by o-ring 308 on open actuator 302, ball bearing 282, and o-ring 310. Of note, the sealed interface between piston 312 and shoulder 306S provided by o-ring 310 may isolate vent hole 324 from the fluid path.

Referring to FIG. 24, some example manifold assemblies 200 including integrated spool valve assemblies 400 as illustrated in FIGS. 15-22 may be placed in an open position in which detent 406 of open actuator 302 may be engaged by ball 320 (see FIG. 16) and open button 402 may be substantially within fifth section 306E. End 412 of open actuator may extend through fourth, narrow section 306D of channel 306, thereby pressing face 414 of piston 312 away from shoulder 306S. In this position, o-ring 310 may not provide a sealed interface between piston 312 and shoulder 306S; thus, vent hole 324 may be fluidically connected to cavity 265 via third section 306C, fourth, narrow section 306D, fifth section 306E, and passage 264. Similarly, vent hole 324 may be fluidically connected to fitting 280 (see FIG. 16) via third section 306C, fourth, narrow section 306D, fifth section 306E, and opening 318 (see FIG. 16). In this open position, cavity 265 may remain fluidically connected to fitting 280 (see FIG. 16) via passage 264, fifth section 306E, and opening 318 (see FIG. 16).

Some example manifold assemblies 200 including integrated spool valve assemblies 400 as illustrated in FIGS. 15-24 may be shifted to the open position as follows. Beginning in the shut position (see FIG. 23 in which vent hole 324 is fluidically isolated from cavity 265), a user may press open button 402. Pressing open button 402 of open actuator 302 with sufficient force to overcome the retaining effect of ball 320 (see FIG. 16) in detent 408 may cause open actuator 302 to move axially within channel 306 towards shut button 304. Once detent 406 is substantially aligned with ball 320, ball 320 may engage detent 406, which may retain spool valve assembly 400 in the open position. In the open position, vent hole 324 may be fluidically connected to cavity 265 as described below in connection with FIG. 24.

Some example manifold assemblies 200 including integrated spool valve assemblies 400 as illustrated in FIGS. 15-24 may be shifted to the shut position as follows. With spool valve assembly 400 in the open position (see FIG. 24), a user may press shut button 304. Pressing shut button 304 with sufficient force to overcome the retaining effect of ball 320 (see FIG. 16) in detent 406 may cause open actuator 302 to move axially within channel 306 towards open button 402. Once detent 408 is substantially aligned with ball 320, ball 320 may engage detent 408, which may retain spool valve assembly 400 in the shut position.

Some example manifold assemblies 200 including integrated spool valve assemblies 400 as illustrated in FIGS. 15-24 may be utilized as part of an elevated vacuum locking system as described herein as follows. The amputee may don flexible liner 50 over her residual limb 2. She may place and/or check spool valve assembly 400 in the open position (see FIG. 24). She may insert the residual limb 2 into the socket 20, allowing the plunger pin 40 to enter the locking mechanism 30. Air displaced by the insertion of residual limb 2 into socket 20 may be vented via any gaps present between liner 50 and the proximal end of socket 20 and/or via vent hole 324. Once plunger pin 40 is at least partially engaged with locking mechanism 30 (e.g., as indicated by at least one perceptible "click" due to locking mechanism 30 engaging with ratchet portion 42 of plunger pin), the amputee may shift spool valve assembly 400 to the shut position (see FIG. 23). Then, the amputee may activate vacuum device 70 to withdraw air via fitting 280. Withdrawing air may cause residual limb 20 to seat within socket 20. Vacuum device 70 may be operated as necessary (e.g., automatically and/or manually) to maintain the desired vacuum within socket 20.

To remove the prosthesis, the amputee may turn off vacuum device 70. The amputee may shift spool valve assembly 400 to the open position (see FIG. 24), thereby allowing air to enter socket 20 via vent hole 324. The amputee may withdraw her residual limb 2 from socket 20 by releasing the locking mechanism 30 (such as by depressing or withdrawing a pin which disengages a latch from ratchet portion 42 of plunger pin 40).

Some example manifold assemblies 200 including integrated spool valve assemblies 400 as illustrated in FIGS. 15-24 may be utilized in connection with elevated vacuum locking systems including sealing sleeves 99 at the proximal end of socket 20 as discussed above. Some example manifold assemblies 200 including integrated spool valve assemblies 400 as illustrated in FIGS. 15-24 may be utilized in connection with elevated vacuum locking systems without sealing sleeves 99, such as elevated vacuum locking systems utilizing a sealing sheath disposed within socket 20 to provide a sealed interface between socket 20 and liner 50. In some such embodiments, it may be impractical to break the sealed interface provided by the sealing sheath due to its location within the socket. Thus, in some such embodiments, vent hole 324 may provide substantially the only air inlet for use while doffing the prosthesis.

Some example manifold assemblies 200 including integrated spool valve assemblies 400 as illustrated in FIGS. 15-24 may be provided with pyramids and/or pyramid receivers as illustrated in FIGS. 12 and 13 and as described above.

Figure 25:
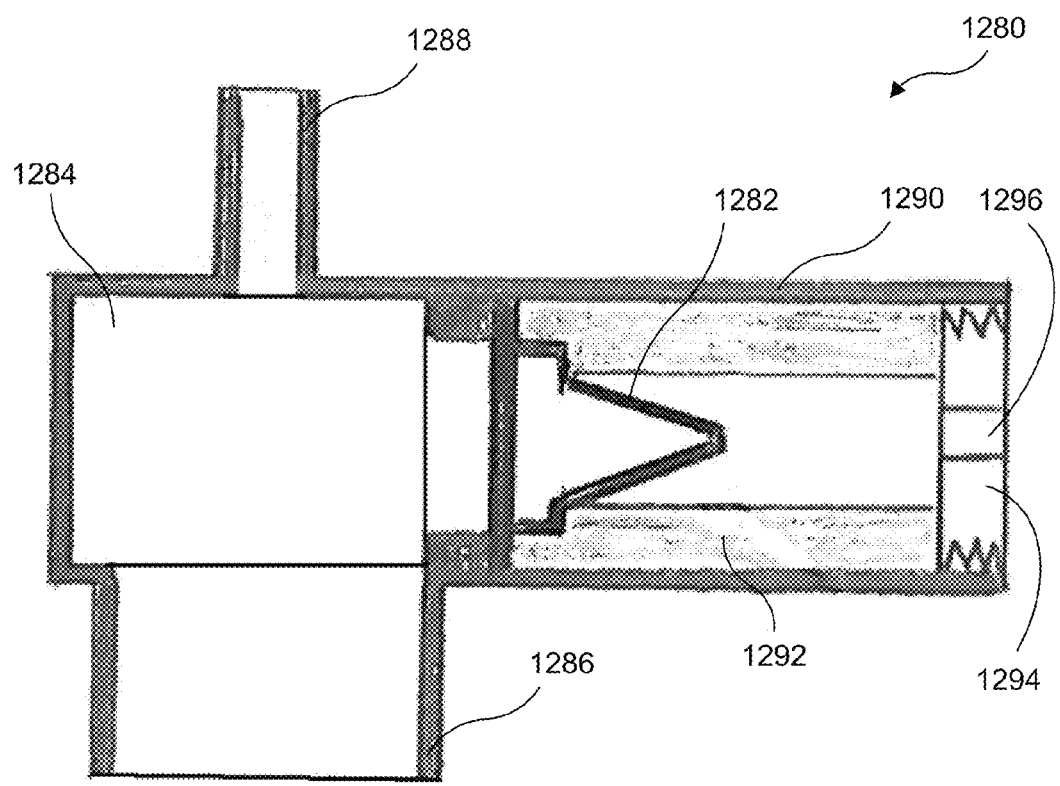
FIG. 25 is a cross-sectional view of a fitting including a duck bill valve for use with an external vacuum source.

Some example embodiments may include a check valve, such as a duck bill valve, which may be configured to allow venting of air while spool valve assembly 400 is in the shut position while still preventing entry of air into socket 20. For example, FIG. 25 illustrates an example fitting 1280 that may be used in place of fitting 280 (see, e.g., FIG. 16). Like fitting 280 described above, fitting 1280 may be seated within opening 318 of valve housing 203, fitting 1280 may house spring 322 arranged to bias a ball 320 towards channel 306, and/or fitting 1280 may extend generally orthogonally relative to distal side 261B of manifold 201.

Referring to FIG. 25, fitting 1280 may include a duck bill valve 1282 (or any other appropriate one-way valve known to those of skill in the art) oriented to allow air to vent from the interior 1284 of fitting 1280 to the ambient environment. Fitting 1280 may include a generally cylindrical, hollow extension 1286 for seating within opening 318 of valve housing 203 (FIG. 16) and/or a generally cylindrical, hollow extension 1288 for coupling with a conduit connecting to a vacuum device. Extension 1286 and/or extension 1288 may be fluidicly connected to interior 1284 of fitting 1280 and/or may be arranged generally axially with respect to fitting 1280. Duck bill valve 1282 may be mounted within a laterally extending valve section 1290, which may be fluidicly connected to interior 1284 of fitting 1280, such as between extension 1286 and extension 1288. Duck bill valve 1282 may be held in place within valve section 1290 by a generally cylindrical, hollow retainer 1292, which may be installed generally axially within valve section 1290. Retainer 1292 may be held in place within valve section 1290 by a threaded cap 1294, which may include a through-hole 1296 and/or which may be installed in the laterally opening end of valve section 1290.

Fitting 1280 including duck bill valve 1282 may operate as follows. When pressure in interior 1284 of fitting 1280 exceeds the ambient pressure, air may flow through duck bill valve 1282 from interior 1284 through through-hole 1296 in cap 1294. Duck bill valve 1282 may substantially prevent air from entering interior 1284 via through-hole 1296 in cap 1294. As will be understood from the description above and FIGS. 23 and 24, fitting 1280 (like fitting 280) remains fluidicly connected to cavity 265 regardless of the position of spool valve assembly 400. Thus, pressure within socket 20 (FIG. 1) may be vented via duck bill valve 1282 regardless of whether spool valve assembly 400 is open or shut.

Figure 26:
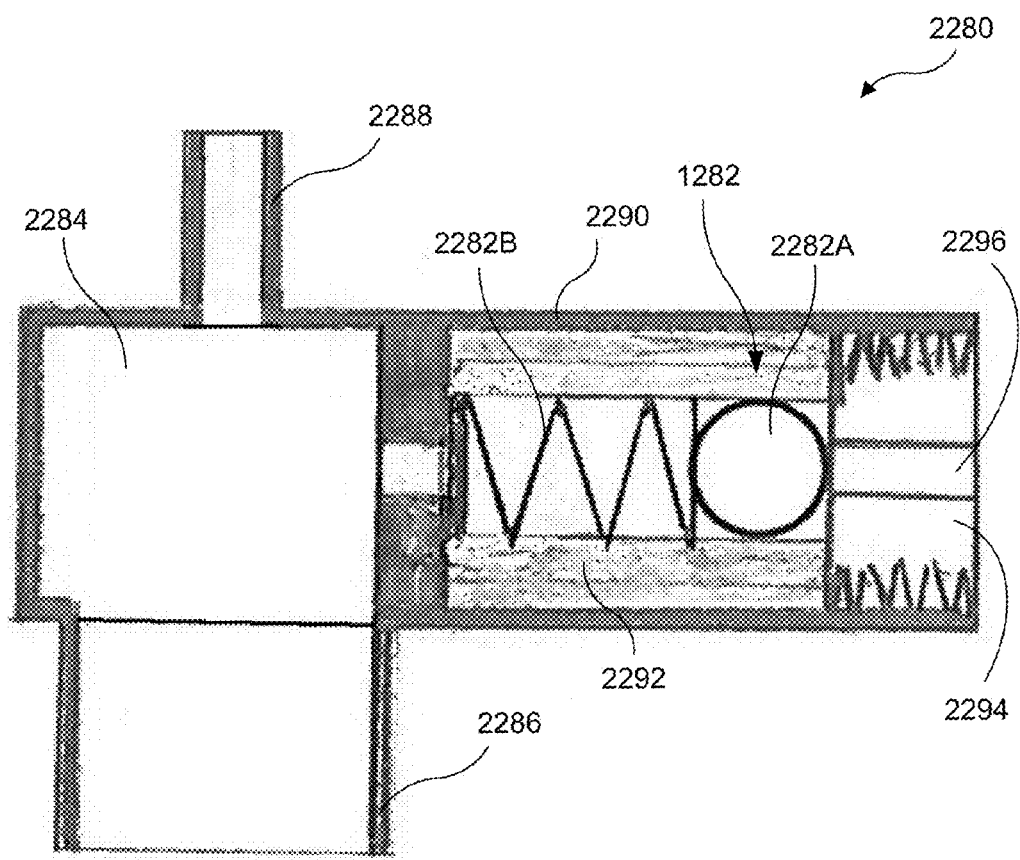
FIG. 26 is a cross-sectional view of a fitting including a ball check valve.

Referring to FIG. 26, some example embodiments may include a fitting 2280 including a pressure/vacuum regulating valve 2282, which may be adjustable to help maintain desired vacuum levels (e.g., 0 to 27 in Hg) in socket 20. For example, fitting 2280 may be used in place of fitting 280 or fitting 1280 as described above (see, e.g., FIG. 16). Like fitting 280 and/or fitting 1280 described above, fitting 2280 may be seated within opening 318 of valve housing 203, fitting 2280 may house spring 322 arranged to bias a ball 320 towards channel 306, and/or fitting 2280 may extend generally orthogonally relative to distal side 261B of manifold 201.

Referring to FIG. 26, fitting 2280 may include a spring-biased ball check valve 2282 (or any other appropriate one-way valve known to those of skill in the art) oriented to allow air to enter the interior 2284 of fitting 2280 from the ambient environment. Fitting 2280 may include a generally cylindrical, hollow extension 2286 for seating within opening 318 of valve housing 203 (FIG. 16) and/or a generally cylindrical, hollow extension 2288 for coupling with a conduit connecting to a vacuum device. Extension 2286 and/or extension 2288 may be fluidicly connected to interior 2284 of fitting 2280 and/or may be arranged generally axially with respect to fitting 2280. Ball check valve 2282 may be mounted within a laterally extending valve section 2290, which may be fluidicly connected to interior 2284 of fitting 2280, such as between extension 2286 and extension 2288. Ball check valve 2282 may be held in place within valve section 2290 by a generally cylindrical, hollow retainer 2292, which may be installed generally axially within valve section 2290. Retainer 2292 and/or ball check valve 2282 may be held in place within valve section 2290 by a threaded cap 2294, which may include a through-hole 2296 and/or which may be installed in the laterally opening end of valve section 2290.

Ball check valve 2282 may include a ball 2282A (e.g., a rubber ball) which may be biased towards cap 2294 by a spring 2282B (e.g., a helical coil compression spring). When the pressure difference between the ambient environment and the pressure in interior 2284 of fitting 2280 is small, the force applied by spring 2282B may be sufficient to substantially seal ball 2282A against cap 2294, thereby substantially preventing air flow through through-hole 2296. When the pressure difference between the ambient environment and the pressure in interior 2284 of fitting 2280 is sufficient to overcome the force of spring 2282B (e.g., a high-vacuum condition within the socket), ball 2282A may unseal from cap 2294, thereby allowing air to enter fitting 2280 via through-hole 2296. Selecting particular components of ball check valve 2282 (e.g., a spring 2282B having a particular spring constant) may allow the pressure differential necessary to open ball check valve 2282 to be determined. For example, a particular spring 2282B providing a lifting pressure differential of 27 in Hg may be utilized to limit the vacuum within socket 20 to about 27 in Hg. Some example embodiments may be adjustable with respect to the lift pressure of ball check valve 2282, such as by accepting springs 2282B having different spring constants and/or by permitting adjustment of the position of cap 2294 axially within valve section 2290. This feature may allow better fitting of a prosthetic device for a greater range of prosthetic users because some vacuum devices 70 may not be configured to provide adjustable vacuum levels.

Figure 27:
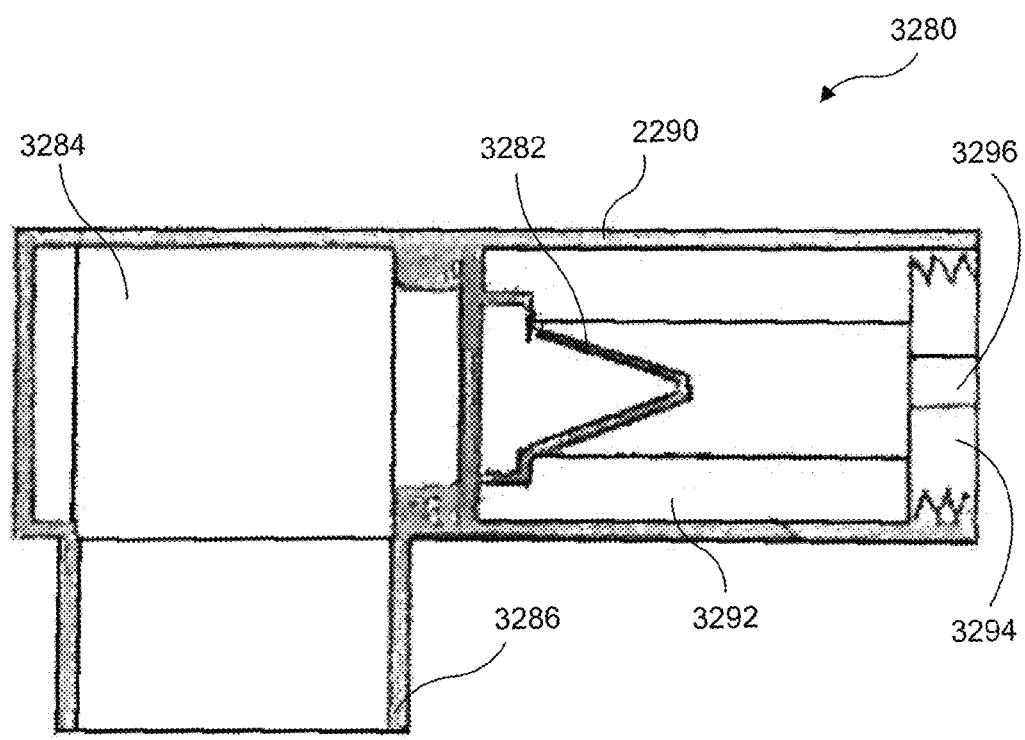
FIG. 27 is a cross-sectional view of a fitting including a duck bill valve for use with a passive vacuum prosthetic socket assembly; all in accordance with at least some examples of the present disclosure.

FIG. 27 illustrates an example fitting 3280 that is generally similar to fitting 1280 of FIG. 25, except that fitting 3280 may not include hollow extension 1288 for coupling with a conduit connecting to a vacuum device. Fitting 3280 may be used, for example, in embodiments that do not include a vacuum device 70. Fitting 3280 may be configured to allow venting of air while spool valve assembly 400 is in the shut position while still preventing entry of air into socket 20. Like fitting 280 described above, fitting 3280 may be seated within opening 318 of valve housing 203, fitting 3280 may house spring 322 arranged to bias a ball 320 towards channel 306, and/or fitting 3280 may extend generally orthogonally relative to distal side 261B of manifold 201.

Fitting 3280 may include a duck bill valve 3282 (or any other appropriate one-way valve known to those of skill in the art) oriented to allow air to vent from the interior 3284 of fitting 3280 to the ambient environment. Fitting 3280 may include a generally cylindrical, hollow extension 3286 for seating within opening 318 of valve housing 203 (FIG. 16). Extension 3286 may be fluidicly connected to interior 3284 of fitting 3280 and/or may be arranged generally axially with respect to fitting 3280. Duck bill valve 3282 may be mounted within a laterally extending valve section 3290, which may be fluidicly connected to interior 3284 of fitting 3280. Duck bill valve 3282 may be held in place within valve section 3290 by a generally cylindrical, hollow retainer 3292, which may be installed generally axially within valve section 3290. Retainer 3292 may be held in place within valve section 3290 by a threaded cap 3294, which may include a through-hole 3296 and/or which may be installed in the laterally opening end of valve section 3290. Fitting 3280 including duck bill valve 3282 may operate substantially the same as fitting 1282 (FIG. 25) described above.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A prosthetic limb assembly comprising:
   a flexible liner shaped to accept a portion of a patient's residual limb, the flexible liner including an interior and an exterior;
   a plunger pin mounted to a distal end of the flexible liner, the plunger pin including at least one through passage providing fluidic communication between a location proximate the exterior of the liner and a distal end of the plunger pin;
   a socket shaped to receive the liner and the patient's residual limb, the socket including a socket interior, a proximal opening for receiving the residual limb, and a distal end including a through hole;
   a locking mechanism mounted within the distal end of the socket and including a central opening sized to receive the plunger pin, the locking mechanism releasably engaging the plunger pin when the residual limb and the liner are inserted into the socket;
   a manifold mounted to the exterior of the distal end of the socket, the manifold including
      a cavity aligned with the through hole in the distal end of the socket, the cavity being adapted to receive the distal end of the plunger pin when the patient's residual limb and the liner are installed into the socket, and
      a through passage fluidicly connecting an interior of the cavity to a fitting mounted on an exterior of the manifold; and
   a spool valve arranged to selectively vent the cavity to an ambient atmosphere via the through passage and a vent hole, the spool valve being axially slidable between an open position and a shut position within a channel provided in a valve housing integrally formed with the manifold to selectively vent the cavity via the vent hole and fluidicly isolate the cavity from the vent hole;
   wherein the fitting is configured to be connected to a vacuum pump for withdrawing air from the interior of the socket via the through passage of the plunger pin, the cavity, and the through passage of the manifold.

2. The prosthetic limb assembly of claim 1,
   wherein the spool valve comprises an open button and a shut button;
   wherein pressing the open button slides the spool valve to the open position; and
   wherein pressing the shut button slides the spool valve to the shut position.

3. The prosthetic limb assembly of claim 1, wherein the spool valve comprises an open actuator including a first detent configured to engage a spring-biased ball when the spool valve is in the open position and a second detent configured to engage the spring-biased ball when the spool valve is in the shut position.

4. The prosthetic limb assembly of claim 1, wherein the spool valve comprises a piston including a face arranged to form a sealed interface with the channel when the spool valve is in the shut position.

5. The prosthetic limb assembly of claim 4, wherein the spool valve comprises an open actuator including an extension arranged to press against the face of the piston to prevent the face from forming the sealed interface when the spool valve is in the open position.

6. The prosthetic limb assembly of claim 1, wherein the valve housing is monolithically integrated with the manifold.

7. The prosthetic limb assembly of claim 1, further comprising at least one fastener extending through the manifold, through the socket wall, and into the locking mechanism.

8. The prosthetic limb assembly of claim 1, wherein the fitting includes a one-way valve oriented to permit air to vent from an interior of the fitting to the ambient atmosphere and to prevent air from entering the interior of the fitting from the ambient atmosphere.

9. The prosthetic limb assembly of claim 1, wherein the fitting includes a one-way valve oriented to permit air to enter an interior of the fitting from the ambient atmosphere when a pressure differential between the ambient atmosphere and the interior of the fitting exceeds a setpoint.

* * * * *